US012735670B2

(12) United States Patent
Parsons et al.

(10) Patent No.: US 12,735,670 B2
(45) Date of Patent: Sep. 15, 2026

(54) SUPPORT STRUCTURES FOR AUTOMATED CELL ENGINEERING SYSTEMS

(71) Applicant: OCTANE BIOTECH INC., Kingston (CA)

(72) Inventors: Scott Parsons, Kingston (CA); Mike Loveless, Kingston (CA); Kevin Meric, Kingston (CA); Wes Chamberlin, Kingston (CA); Robert Magyar, Kingston (CA); Michael Nuttall, Kingston (CA); Ammar Al-Dojaily, Kingston (CA); Rade Gadzic, Kingston (CA)

(73) Assignee: OCTANE BIOTECH INC., Kingston (CA)

( * ) Notice: Subject to any disclaimer, the term of this patent is extended or adjusted under 35 U.S.C. 154(b) by 820 days.

(21) Appl. No.: 18/158,213

(22) Filed: Jan. 23, 2023

(65) Prior Publication Data

US 2023/0235268 A1 Jul. 27, 2023

Related U.S. Application Data

(60) Provisional application No. 63/302,366, filed on Jan. 24, 2022.

(51) Int. Cl.

*C12M 1/36* (2006.01)
*C12M 1/00* (2006.01)

(Continued)

(52) U.S. Cl.

CPC ............ *C12M 41/48* (2013.01); *C12M 23/44* (2013.01); *C12M 23/48* (2013.01); *C12M 29/08* (2013.01); *C12M 41/12* (2013.01); *C12M 41/34* (2013.01)

(58) Field of Classification Search

None

See application file for complete search history.

(56) References Cited

U.S. PATENT DOCUMENTS

| | | | |
|---|---|---|---|
| 4,939,151 | A | 7/1990 | Bacehowski et al. |
| 5,424,209 | A | 6/1995 | Kearney |

(Continued)

FOREIGN PATENT DOCUMENTS

| | | | |
|---|---|---|---|
| KR | 20000023786 | U | 9/2001 |
| WO | 97/12960 | A2 | 4/1997 |

(Continued)

OTHER PUBLICATIONS

Aitken-Christie et al., Automation in Plant tissue culture—general introduction and overview, in Automation and Environmental Control in Plant Tissue Culture 757 (J. Aitken-Christie, T. Kozai & M. Lila Smith eds., 1995).

(Continued)

*Primary Examiner* — Holly Kipouros

(74) *Attorney, Agent, or Firm* — MEDLER FERRO WOODHOUSE & MILLS PLLC

(57) ABSTRACT

The present technology is generally related to storage structures for cell engineering systems. The storage structures allow for multiple automated cell engineering systems to be held via a single structure, and presented to a user when desired or needed for direct access to the cell engineering system, and then returned to a storage or working position. Many storage structures can be arranged together in a clinical or hospital setting, or other cell therapy engineering manufacturing environment.

9 Claims, 22 Drawing Sheets

(51) Int. Cl.
*C12M 1/34* (2006.01)
*C12M 3/00* (2006.01)

(56) References Cited

U.S. PATENT DOCUMENTS

| | | | | |
|---|---|---|---|---|
| 5,478,479 | A | 12/1995 | Herrig | |
| 5,985,653 | A | 11/1999 | Armstong et al. | |
| 5,989,913 | A | 11/1999 | Anderson et al. | |
| 5,994,129 | A | 11/1999 | Armstrong et al. | |
| 6,048,721 | A | 4/2000 | Armstrong et al. | |
| 6,048,722 | A | 4/2000 | Farb et al. | |
| 6,096,532 | A | 8/2000 | Armstrong et al. | |
| 6,123,655 | A | 9/2000 | Fell | |
| 6,197,575 | B1 | 3/2001 | Griffith et al. | |
| 6,214,574 | B1 | 4/2001 | Kopf | |
| 6,228,635 | B1 | 5/2001 | Armstrong et al. | |
| 6,238,908 | B1 | 5/2001 | Armstrong et al. | |
| 6,297,046 | B1 | 10/2001 | Smith et al. | |
| 6,402,941 | B1 | 6/2002 | Lucido et al. | |
| 7,906,323 | B2 | 3/2011 | Cannon et al. | |
| 9,629,877 | B2 | 4/2017 | Cooper et al. | |
| 10,131,876 | B2 | 11/2018 | Kaiser et al. | |
| 10,253,316 | B2 | 4/2019 | Masquelier et al. | |
| 10,273,300 | B2 | 4/2019 | Bedoya et al. | |
| 2001/0021529 | A1 | 9/2001 | Takagi | |
| 2002/0025547 | A1 | 2/2002 | Rao | |
| 2002/0179525 | A1 | 12/2002 | Shaffer et al. | |
| 2008/0160591 | A1 | 7/2008 | Willson et al. | |
| 2010/0316446 | A1* | 12/2010 | Runyon | C12M 41/48 435/243 |
| 2015/0140653 | A1 | 5/2015 | Jones et al. | |
| 2015/0344844 | A1 | 12/2015 | Better et al. | |
| 2016/0122782 | A1 | 5/2016 | Crisman et al. | |
| 2017/0037369 | A1 | 2/2017 | Ramsborg et al. | |
| 2017/0051252 | A1 | 2/2017 | Morgan et al. | |
| 2017/0341873 | A1 | 11/2017 | Vivet et al. | |
| 2018/0104697 | A1* | 4/2018 | Butler | C12M 23/48 |
| 2019/0017009 | A1 | 1/2019 | Yu | |
| 2019/0211294 | A1 | 7/2019 | Karnieli | |
| 2020/0131460 | A1 | 4/2020 | Higuchi et al. | |
| 2020/0200781 | A1 | 6/2020 | Smith et al. | |
| 2021/0095239 | A1* | 4/2021 | Recker | C12M 23/44 |
| 2021/0246406 | A1* | 8/2021 | Roberts | C12M 21/06 |

FOREIGN PATENT DOCUMENTS

| | | | |
|---|---|---|---|
| WO | 99/47922 | A2 | 9/1999 |
| WO | 01/00783 | A2 | 1/2001 |
| WO | 2015/162211 | A1 | 10/2015 |
| WO | 2016/069993 | A1 | 5/2016 |
| WO | 2016/118780 | A1 | 7/2016 |
| WO | 2016/168275 | A1 | 10/2016 |
| WO | 2017/068425 | A1 | 4/2017 |
| WO | 2018/015561 | A1 | 1/2018 |
| WO | 2018/136566 | A1 | 7/2018 |

OTHER PUBLICATIONS

Apel et al., Integrated Clinical Scale Manufacturing System for Cellular Products Derived by Magnetic Cell Separation, Centrifugation and Cell Culture, Chemie Ingenieur Technik (2013).

Armstrong et al., Clinical Systems for the Production of Cells and Tissues for Human Therapy, in Novel Therapeutics From Modern Biotechnology 221 (D.L. Oxender et al. eds., 1999).

Blaeschke et al., Induction of a Central Memory and Stem Cell Memory Phenotype in Functionally Active CD4+ and CD8+ CAR T Cells Produced in an Automated Good Manufacturing Practice System for the Treatment of CD19+ Acute Lymphoblastic Leukemia, Cancer Immunology, Immunotherapy vol. 67, pp. 1053-1066 (2018), published Mar. 31, 2018.

Bohnenkamp et al., Bioprocess development for the cultivation of human T-lymphocytes in a clinical scale, Cytotechnology (2002).

Bousso, T-cell activation by dendritic cells in the lymph node: lessons from the movies, 8 Nature Reviews Immunology 675 (2008) (“Bousso 2008”).

Kaiser et al., Towards a Commercial Process for the Manufacture of Genetically Modified T Cells for Therapy, 22 Cancer Gene Therapy 72-78 (2015).

Kempner et al., A Review of Cell Culture Automation, 7 Journal of the Association for Laboratory Automation 56 (2002) (“Kempner 2002”).

Koller et al., Clinical-scale human umbilical cord blood cell expansion in a novel automated perfusion culture system, Bone Marrow Transplantation (1998) (“Koller 1998”).

Koller et al., Large-Scale Expansion of Human Stem and Progenitor Cells from Bone Marrow Mononuclear Cells in Continuous Perfusion Cultures, Blood (1993) (“Koller 1993A”).

Koller et al., Tissue Engineering: Reconstitution of Human Hematopoiesis Ex Vivo, Biotechnology and Bioengineering (1993) (“Koller 1993B”).

Kostov et al., Low-Cost Microbioreactor for High-Throughput Bioprocessing, 72 Biotechnology and Bioengineering, Feb. 5, 2001 (“Kostov 2001”).

Krug et al., A GMP-compliant protocol to expand and transfect cancer patient T cells with mRNA encoding a tumor-specific chimeric antigen receptor, Cancer Immunol Immunotherapy (2014) (“Krug 2014”).

Levine et al., Global Manufacturing of CAR T Cell Therapy, 4 Molecular Therapy: Methods & Clinical Development 92 (2017).

Lock et al., Automated Manufacturing of Potent CD20-Directed Chimeric Antigen Receptor T Cells for Clinical Use, 28 Human Gene Therapy 10 (2017), (“Lock 2017”).

Lu et al., A Rapid Cell Expansion Process for Production of Engineered Autologous CART Cell Therapies, 27 Human Gene Therapy 6 (2016).

Mock et al., Automated manufacturing of chimeric antigen receptor T cells for adoptive immunotherapy using CliniMACS Prodigy, Cytotherapy (2016).

Morse, Technology evaluation: Stem-cell therapy, Aastrom Biosciences Inc., Current Opinion in Molecule Therapeutics (1999) (“Morse 1999”).

Oh et al., Frequent Harvesting from Perfused Bone Marrow Cultures Results in Increased Overall Cell and Progenitor Expansion, Biotechnology and Bioengineering (1994).

Priesner et al., Automated Enrichment, Transduction, and Expansion of Clinical-Scale CD62L+ T Cells for Manufacturing of Gene Therapy Medicinal Products, 27 Human Gene Therapy 10, 860-869 (2016).

Rosazza et al., Gene Electrotransfer: A Mechanistic Perspective, Current Gene Therapy (2016) (“Rosazza 2016”).

Shi et al., “Performance of Mammalian Cell Culture Bioreactor with a New Impeller Design” Biotechnology and Bioengineering, vol. 40, pp. 260-270 (1992).

Stiff et al., Autologous transplantation of ex vivo expanded bone marrow cells grown from small aliquots after high-dose chemotherapy for breast cancer, Blood (2000) (“Stiff 2000”).

Wang et al., Clinical Manufacturing of CAR T Cells: Foundation of a Promising Therapy, 3 Molecular Therapy—Oncolytics 1 (2016).

Wang et al., Manufacture of Tumor- and Virus-specific T Lymphocytes for Adoptive Cell Therapies, 22 Cancer Gene Therapy 2 (2015).

Zhang et al., Characterization of clinical grade CD19 chimeric antigen receptor T cells produced using automated CliniMACS Prodigy system, Drug Design, Development and Therapy (2018) (“Zhang 2018”).

Zhu et al., Closed-system manufacturing of CD19 and dual-targeted CD20/19 chimeric antigen receptor T cells using the CliniMACS Prodigy device at an academic medical center, Cytotherapy (2018).

Basic and Clinical Immunology: Antigen Presentation, T Cell Activation and Deactivation, Clevelandcliniccme, found at https://www.youtube.com/watch?v=EfYpkA4AmFo (2017), last visited Dec. 6, 2020 (“Cleveland Clinic video”).

* cited by examiner

SUPPORT STRUCTURES FOR AUTOMATED CELL ENGINEERING SYSTEMS

CROSS-REFERENCE TO RELATED APPLICATIONS

The present application claims benefit of U.S. Provisional Patent Application No. 63/302,366, filed Jan. 24, 2022, the disclosure of which is incorporated by reference herein in its entirety.

FIELD

The present technology is generally related to storage structures for cell engineering systems. The storage structures allow for multiple automated cell engineering systems to be held via a single structure, and presented to a user when desired or needed for direct access to the cell engineering system, and then returned to a storage or working position. Many storage structures can be arranged together in a clinical or hospital setting, or other cell therapy engineering manufacturing environment.

BACKGROUND

Existing engineering robotic systems for automated cell culture processes are complex, require significant laboratory space for operation, and represent a substantial capital equipment investment.

Equipment design is frequently recognized as a key component in the success of GMP (Good Manufacturing Practice) biologics manufacturing but is not always implemented with full appreciation of the processing implications. In the case of mammalian cell culture, there are recognized issues and risks that develop when transitioning to a large, automated scale of operation. The developing demand for cell culture production capacity in the biopharmaceutical industry has led to an increase in the scale of automated operation.

There is also a growing demand for patient-specific treatments, such as for autologous cell therapy. Autologous cell therapy requires complex multiple concurrent processing events placing considerably more demands with respect to automation. Automated production units may only service one patient at any given production cycle. Scaling for large parallel processing for large numbers of patients generates the need for developing space-efficient organization and access to multiple production units within a production facility.

Accordingly, it is desirable to develop ways to achieve maximized cell production in existing production facility confines. Further, it is desirable to develop ways to achieve maximized cell production in existing production facility confines that does not detrimentally affect the integrity of the cell culture systems. It is also desired to improve ergonomics for users of automated cell and tissue engineering systems. The present invention fulfills these desires.

SUMMARY

In an embodiment, an automated selection and support system is provided. The automated selection and support system may include a plurality of biologic processing units, where each of the plurality of biologic processing units may be translatable between a first position for storage and maintaining the plurality of biologic processing units, and a second position for presenting at least one or more of the plurality of biologic processing units. A movable support structure may be provided for transitioning each of the plurality of automated biologic processing units between the first position and the second position. An electrical system may include a power supply and an interface device, with both the power supply and the interface device being operatively connected to each of the plurality of automated biologic processing units and the movable support structure. A gas supply system may include a gas line fluidly coupled to each of the plurality of automated biologic processing units.

In another embodiment, an automated selection and support system is provided. The automated selection and support system may include a plurality of automated biologic processing units, where each of the plurality of automated biologic processing units may have a first position for storage and maintaining the plurality of automated biologic processing units, and a second position for presenting the automated biologic processing unit to a user. A plurality of swing arms may be provided, and each swing arm may include a first end operatively coupled to one automated biologic processing unit from the plurality of automated biologic processing units, and a second end operatively coupled to a drive motor. The drive motor may be configured to rotate the swing arm to transition the automated biologic processing unit between the first position and the second position. The swing arm may maintain the automated biologic processing unit rotationally level. An electrical system may include a power supply and an interface device, both operatively coupled to each of the automated biologic processing units and the drive motor. A gas supply system may include a gas line fluidly coupled to each of the plurality of automated biologic processing units.

In another embodiment, an automated selection and support system is provided. The automated selection and support system may include a plurality of automated biologic processing units, where each of the plurality of automated biologic processing units may have a first position for storage and maintaining the plurality of automated biologic processing units, and a second position for presenting the automated biologic processing unit to a user. The automated selection and support system may include a plurality of vertical rails. It may also include a gantry configured to move on the vertical rails and select one of the automated biologic processing units and transition the automated biologic processing unit between the first position and the second position. An electrical system may include a power supply and an interface device both operatively coupled to each of the automated biologic processing units. A gas supply system may include a gas line fluidly coupled to each of the plurality of automated biologic processing units. The vertical rails, the electrical system, the gas supply system, and/or a heat management system may all be enclosed within a housing.

In another embodiment, an automated selection and support system is provided. The automated selection and support system may include a plurality of automated biologic processing units, where each of the plurality of automated biologic processing units may have a first position for storage and maintaining the plurality of automated biologic processing units, and a second position for presenting the automated biologic processing unit to a user. A plurality of modular holding cells may be configured to each hold one of the automated biologic processing units. A shuttle may be configured to travel between each of the modular holding cells to select one of the automated biologic processing units and transition the automated biologic processing unit between the first position and the second position. An electrical system may include a power supply and an interface device, both operatively coupled to each of the automated biologic processing units. A gas supply system may include a gas line fluidly coupled to each of the plurality of automated biologic processing units. The electrical system, the gas supply system, and/or a heat management system may be enclosed within a housing.

In another embodiment, an automated selection and support system is provided. The automated selection and support system may include a plurality of automated biologic processing units, where each of the plurality of automated biologic processing units may have a first position for storage and maintaining the plurality of automated biologic processing units, and a second position for presenting the automated biologic processing unit to a user. A plurality of transfer blocks may be provided, where each transfer block may be configured to couple to an automated biologic processing unit of the plurality of automated biologic processing units. A coupler may be configured to mate with one of the blocks of the plurality of blocks. A first track may be configured to move the coupler in a first direction. A second track may be configured to move the first track in a second direction, wherein the second track is substantially perpendicular to the first track. An electrical system may include a power supply and an interface device, both operatively connected to each of the plurality of automated biologic processing units and the transfer blocks. A gas supply system may include a gas line fluidly coupled toe ach of the plurality of automated biologic processing units. The first track and second track may be configured to move one of the plurality of automated biologic processing units from the first position to the second position.

In another embodiment, a method for presenting an automated biologic processing unit to a user is provided. The method may comprise the steps of: selecting an automated biologic processing unit from an automated selection and storage system, the automated selection and storage system including: a plurality of automated biologic processing units, each of the plurality of automated biologic processing units having a first position for storage and maintaining the automated biologic processing units, and a second position for presenting the automated biologic processing unit to a user; a movable support structure for transitioning each of the plurality of automated biologic processing units between the first position and the second position; an electrical system including a power supply and an interface device, both operatively connected to each of the plurality of automated biologic processing units and the movable support structure; and a gas supply system including a gas line fluidly coupled to each of the plurality of automated biologic processing units; transitioning the selected automated biologic processing unit from the first position to the second position using the movable support structure; and returning the selected automated biologic processing unit from the second position to the first position.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the art to make and use the invention. The drawings are not to scale.

DETAILED DESCRIPTION

Figure 1B:
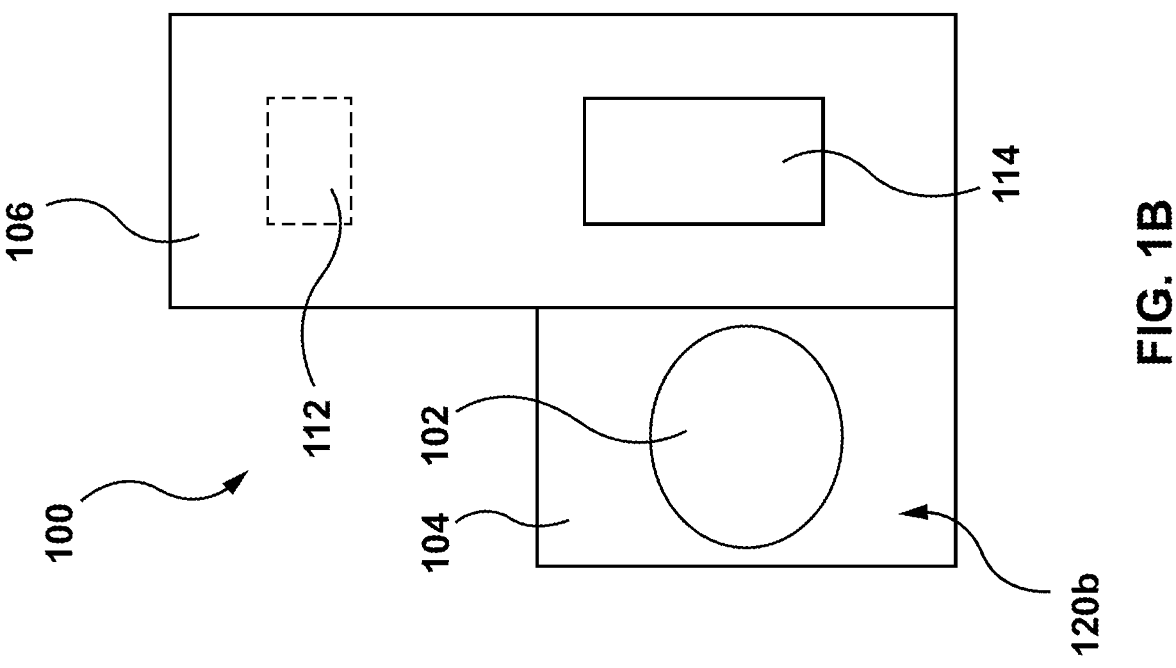
FIG. 1B depicts a schematic view of the automated selection and support system of FIG. 1A in a second position.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise defined herein, scientific and technical terms used in the present disclosure shall have the meanings that are commonly understood by one of ordinary skill in the art. Further, unless otherwise required by context, singular terms shall include pluralities and plural terms shall include the singular.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The use of the term "or" in the claims is used to mean "and/or", unless explicitly indicated to refer only to alternatives or the alternatives are mutually exclusive, although the disclosure supports a definition that refers to only alternatives and "and/or".

As used herein, the term "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited, elements or method steps.

The use of the term "for example" and its corresponding abbreviation "e.g." means that the specific terms recited are representative examples and embodiments of the disclosure that are not intended to be limited to the specific examples referenced or cited unless explicitly stated otherwise.

As used herein, "between" is a range inclusive of the ends of the range. For example, a number between x and y explicitly includes the numbers x and y and any numbers that fall within x and y.

As described herein and throughout the Figures, an automated biologic processing unit 102 is a fully enclosed (i.e., sterility is maintained within the unit via interconnected tubing and elements or containers within the unit), automated system, for performing activating, transducing, expanding, concentrating, and/or harvesting steps, of cell cultures. Automated biologic processing units (also called automated cell engineering systems throughout) provide for the automated production of cell cultures. As used herein "cell cultures" refers to any suitable cell type, including individual cells, as well as multiple cells or cells that may form into tissue structures. Exemplary cell cultures include blood cells, skin cells, muscle cells, bone cells, cells from various tissues and organs, etc.. In embodiments, genetically modified immune cells, including CAR T cells, as described herein, can be produced. Exemplary automated cell engineering systems are also called COCOON™, or COCOON™ system throughout (see e.g., U.S. Published Patent Application No. 2019/0169572, now U.S. Pat. No. 11,447,745, the disclosure of which is incorporated by reference herein in its entirety).

An automated selection and support system 100 is configured to store, maintain, and support the plurality of automated biologic processing units 102. When placed within the automated selection and support system 100, each automated biologic processing unit 102 has a first position 120*a* configured for storage, operation, and maintaining the automated biologic processing unit 102 and a second position 120*b* for presenting one or more of the automated biologic processing units 102 to a user (i.e., a user presentation position). The user may interact with the automated selection and support system 100 in order to individually select the biologic processing units 102, allowing the user to monitor information regarding the biologic processing unit 102 as well as transition the selected biologic processing unit 102 from the first position 120*a* to the second position 120*b*. It should be understood that "first position" and "second position" are used herein solely to indicate two separate positions that can be obtained by the support systems 100, and multiple additional positions can be obtained between the first and second position, as well as before and after obtaining the first and second positions.

In embodiments, the biologic processing units 102 may translate to a plurality of positions, i.e. nth positions, between a first position 120*a* configured for storage and maintaining the automated biologic processing units, and a second position 120*b* for presenting one or more of the automated biologic processing units 102 to a user, where the value n in the nth positions is any number of positions between the first position 120*a* and the last position. For example, the biologic processing units 102 may translate from the first position 120*a* to a first intermediate position between the first position 120*a* and second position 120*b*. The biologic processing units 102 may then translate from the first intermediate position to a third intermediate position between the first intermediate position and second position 120*b*. The biologic processing units 102 may then repeat such translational movements for n number of times until finally translating to the second position 120*b* for presenting the one or more of the biologic processing units 102 to the end user, and may further translate to additional positions before returning to the first position 120*a*. The biologic processing units 102 may also translate to each of the nth positions between the first position 120*a* and second position 120*b*. In embodiments, the first position 120*a*, nth positions, and/or second position 120*bs* may further include an angle of tilt of each of the biologic processing units 102, such that the angle of tilt of at least one of the biologic processing units 102 in the first position 120*a* is dissimilar to the angle of tilt of the same biologic processing unit 102 in an nth position and/or the second position 120*b*. In embodiments, the angle of tilt of at least one of the biologic processing units 102 in the first position 120*a* and second position 120*b* is the same, while the angle of tilt of the same biologic processing unit 102 in an nth position is the same as to that of the first position 120*a* and second position 120*b*, so as to maintain a cell culture within the automated biologic processing unit 102 in a steady manner without significant disturbance. The translational and/or tilt movement of the at least one of the biologic processing units 102 between the first position 120*a* and the second position 120*b* suitably does not impact the activating, transducing, expanding, concentrating, and/or harvesting steps, of cell cultures within the other remaining (i.e. non-translating) biologic processing units 102.

Figure 1A:
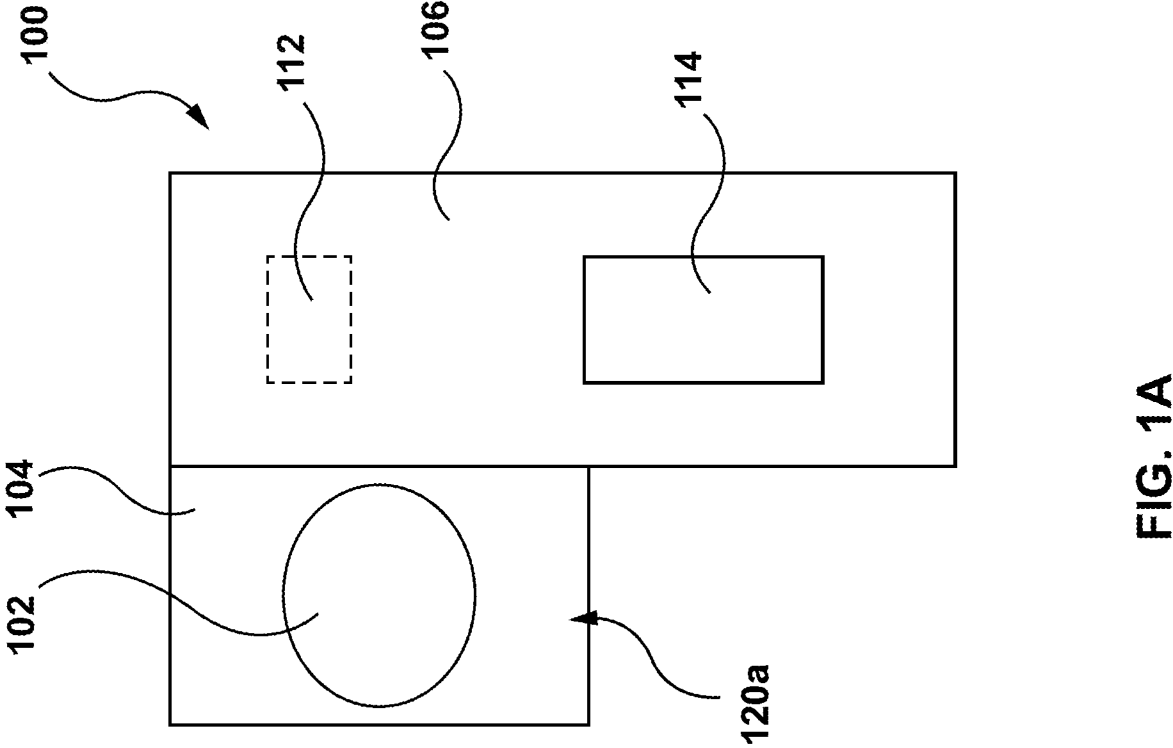
FIG. 1A depicts a schematic view of an automated selection and support system in a first position.

An exemplary automated selection and support system is shown in FIGS. 1A and 1B. The automated selection and support system 100 generally includes a movable support structure 104 and a housing 106 capable of providing resources to each of the biologic processing units 102. The movable support structure 104 is capable of both supporting and transitioning the biologic processing units 102 between the aforementioned first position 120*a* and the second position 120*b*. The first position 120*a* is shown in FIG. 1A is characterized by being the primary position of the biological process unit 102 while in storage and maintenance, allowing for the biological process within each biologic processing unit 102 to be completed. As used herein "storage and maintenance" or "for storage and maintaining" includes instances where the biological process unit 102 is not active or activated (i.e., does not contain cells or other biologic components), as well as instances where the biologic processing unit is active, in that one or more biologic processes (e.g., cell culture, expansion, transfection, etc.) is taking place. While in the first position 120*a*, the automated selection and support system 100 is configured to hold the biologic processing units 102 substantially stable, as to allow each of the biologic processing units 102 to carry on desired biologic processes, or to be in a non-active state. The second position 120*b* is shown in FIG. 2A and may be characterized as allowing the user to have access to the components of the automated biologic processing units 102, allowing for the user to check progress, perform maintenance, introduce or remove various buffers, cells, cell cultures, virus or vector systems, etc.

The movable support structure 104 may be coupled to the housing 106 and either one or the plurality of automated biologic processing units 102. In some embodiments, the movable support structure 104 is configured to move each biologic processing unit 102 between the first position 120*a* and the second position 120*b* while keeping each of the biologic processing units 102 stable. Each biologic processing unit 102 requires a level of stability in order to maintain the laminar state required for reliable function. The movable support structure 104 may achieve the required level of stability by moving the automated biologic processing unit 102 in a way to limit any forces on the unit 102, for example, by eliminating sudden starts and stops, utilizing a constant or substantially constant velocity of movement, etc. Further, it is envisioned, that in some embodiments, the movable support structure 104 may rotate or translate so as to hold each biologic processing unit 102 rotationally level during the transition as to further limit any possible forces negatively effecting each unit 102, such as gravity. In embodiments, the movable support structure 104 may allow for each biologic processing unit 102 to rotate through 360° of rotation with respect to the movable support structure. In embodiments, the movable support structure 104 may allow for each biologic processing unit 102 to rotate through at least 180° of rotation with respect to the movable support structure. Depending on the configuration of the automated selection and support system 100, each automated biologic processing unit 102 may be connected to a dedicated movable support structure 104. In embodiments, a singular moveable support structure 104 may service each of the automated biologic processing units 102.

Exemplary movable support structures 104 include various types of arms, swing-arms, rotating units, track structures, pulley structures, or any other type of translatable support structure capable of translating each of the plurality of biologic processing units 102 as described herein.

The housing 106 may contain all components required for the moveable support structure 104 to transition the automated biologic processing units 102 as well as contain any resources necessary for the automated biologic processing units 102 to function properly. For example, the housing 106 may contain the mechanical components and electrical components necessary to operate numerous moveable support structures 104, such as motors, pulleys, processors, electrical wires, etc. Further, an interface device 114 may be positioned at or on the housing 106, allowing for a user to interact with the systems of the automated selection and support system 100. In embodiments, the interface device may include a graphical user interface (GUI), radio frequency identification (RFID) sensors such as low frequency RFID, high frequency RFID, ultra high frequency RFID, passive RFID (e.g. radio signal responsive), active RFID (e.g. battery powered RFID tags), semi-passive RFID (e.g. battery-assisted RFID tags), wireless identification and sensing platforms (WISP), and any other form of identification sensor technology, a barcode scanner, a camera, fingerprint sensors, optical sensors, multispectral sensors, and/or any other applicable forms of biometric security technologies.

As noted, each of the automated biologic processing units 102 may require access to resources such as electrical, gas, and temperature control systems in order to properly function. These processes may be coupled to the automated biologic processing units 102 internally through the moveable support structures 104 and/or the housing 106 or, in some embodiments, may be positioned externally from the automated selection and support system 100. For example, it is envisioned that a plurality of automated selection and support systems 100 may be positioned within a temperature-controlled room that provides sufficient ventilation to support each of the automated biologic processing units 102. Further details related to electrical, gas, and temperature control systems are described below.

An electrical system 108 may be positioned within the automated selection and support system 100, particularly in the housing 106, to provide support to each of the automated biologic processing units 102. Further, it is envisioned that in some embodiments a singular electrical system 108 may be positioned externally relative to the automated selection and support system 100, wherein the electrical system 108 is capable of being connected to multiple automated selection and support systems 100. The electrical system 108 may be controlled by a central computer system of the automated selection and support system 100 or by an independent computer system specifically configured to control the electrical system 108. The electrical system 108 may either generate power independently (e.g., photovoltaic power, or mechanical power generated through the movements of the movable support structures 104, where the power generated from these examples may be stored on a battery for later use, etc.) or may receive electricity from an external source, for example, through a means such as a wall plug. In some embodiments, the electrical system 108 is configured to control the current and voltage of the electricity provided to the automated biologic processing units 102, as well as monitor the electricity usage of each of the biologic processing units 102 as to provide an independent tailored flow of electricity to each unit 102.

Each of the automated biologic processing units 102 may be independently connected to the electrical system 108 through a series of electrical conduits that may be positioned within the automated selection and support system 100, in particular, the moveable support structure and/or the housing 106. The automated biologic processing units 102 may each be connected to a continuous singular circuit or may each be independently connected to the electrical system 108, as to provide a safeguard as compared to providing a singular circuit.

A gas supply system 110 may be connected to each individual automated biologic processing unit 102 and be positioned within the housing 106 of the automated selection and support system 100. The gas source may be positioned internally to the automated selection and support system 100 in the form of a tank, or the gas may be provided to the gas supply system 110 externally, such as from gas supply lines from a building or laboratory. In some embodiments, the gas supply system 110 is configured to supply a consistent stream of carbon dioxide to each of the automated biologic processing units 102, however, it is envisioned that other gases, such as nitrogen, hydrogen, oxygen, etc., may be used. The gas supply system 110 may be controlled by the central computer system or by an independent computer system specifically configured to control the gas supply system 110.

Each of the automated biologic processing units 102 may also be connected to the gas supply system 110 through a system of conduits that may be positioned within the housing 106 and/or the moveable support structure 104. In some embodiments, a main gas line may be positioned through the housing 106, and a series of auxiliary gas lines may branch off of the main gas line to connect each automated biologic processing unit 102. In some embodiments, the gas supply system 110 may be configured to maintain a consistent gas pressure within the main line and the auxiliary gas lines despite possible variation in gas usage by each of the biologic processing units 102. The gas supply system 110 may further control and monitor the usage of each of the biologic processing units 102 as to provide an independent tailored flow of gas to each unit 102.

In some embodiments, the automated biologic processing units 102 require a consistent temperature (e.g., ±5° C.) in order to operate properly. It is envisioned that each automated biologic processing unit 102 may produce heat, and, in some embodiments, a heat management system 112 may be used to remove heat from each of the automated biologic processing units 102 to cool the units. The heat management system 112 may either be positioned within the housing 106 of the automated selection and support system 100 or be positioned externally of the automated selection and support system 100. For example, multiple automated selection and support systems 100 may be positioned in a temperature-controlled room, wherein the heat management system 112 may be configured to regulate the temperature of the room or provide live data regarding the temperature of the units 102 to an external ventilation system. When positioned internally, the heat management system 112 may use a plurality of fans to either push or pull ambient air across the surface of each of the automated biologic processing units 102. The ambient air may then be regurgitated back into the surrounding ambient air or may be cooled by an internal or external temperature interface device, such as an air conditioner.

In embodiments, the heat management system 112 may comprise a fluid cooled system in which tubing or similar structures run on or near the surface of the automated biologic processing units 102 to cool the units, or can run within the automated biologic processing units 102. For example, tubular structures, hoses, or other liquid impermeable structures designed to allow for the flow of fluid therethrough (not shown) may wrap around, be adjacent to, or be disposed on or within each of the biologic processing units 102. When the temperatures of the biologic processing units 102 are determined to exceed a desired threshold—either manually or automatically via a central computer system—a flow of fluid may be introduced through the fluid impermeable structures. The flow rate of said fluid through the fluid impermeable structures may be based on the differential between the predetermined threshold temperature, and the actual temperature of the biologic processing units 102. For example, if more heat removal (i.e. greater cooling) is desired, then the flow rate of the fluid through the fluid impermeable structures may be higher. If less heat removal is desired, then the flow rate of the fluid through the fluid impermeable structures may be lower.

In embodiments, the heat management system 112 may include a mechanism for controlling condensation generated from the heat removal procedures described herein. For example, if a liquid is flowed through the fluid impermeable structures, the heat management system 112 may further comprise means of ensuring the liquid is maintained above a local dew point (i.e. the temperature to which the surrounding air must be cooled for the liquid to become vapor) relative to the immediate environment and ambient temperature (i.e. the air temperature of the biologic processing unit 102 and relative components, and/or the environment where the biologic processing unit 102 is stored). This may be achieved through a humidity monitoring device/sensor, disposed on or within the biologic processing unit 102, and/or integrated with the heat management system 112.

The heat management system 112, if positioned internally or externally, may be controlled by a central computer system or by an independent computer system specifically configured for the heat management system 112. Further, it is envisioned that the temperature of each of the biologic processing units 102 will be monitored as to provide the user and the computer system with information as to whether the biologic processing unit 102 is falling out of a range of acceptable temperatures and to make any necessary corrections.

The interface device 114 may be positioned on the housing 106 and is configured to provide the user with information relating to each of the biologic processing units 102, the movable support structure 104, the electrical system 108, the gas supply system 110, and the heat management system 112. Further, the interface device 114 may allow the user to independently select each of the automated biological process units 102 as to both monitor the status of the unit 102 and to transition the unit 102 between the first and last positions. The interface device 114 may take the form of an embedded touch screen, internal computer, or may be positioned externally from the housing 116, in the form of a desktop, tablet, or other computing means. The interface device 114 also allows for a user to adjust each of the biologic processing units 102 as to alter the chosen process of the biologic processing unit 102, the electrical current into the unit 102, the gas flow into the unit 102, and the temperature of the unit 102.

In embodiments, information or data relating to each of the biologic processing units 102 may be extracted from each individual biologic processing unit 102 in real time. For example, information pertaining to the position, temperature, electrical supply, gas supply, and/or status of the cells or cell cultures within each individual biologic processing unit 102 may be separately relayed to the interface device 114 or extracted via the interface device 114 for automated analysis and display, in a manner simultaneous to said information being generated. The user adjustment of each biologic processing unit 102 via the interface device 114 may also be achieved in real time, and separately with regards to each biologic processing unit 102.

In embodiments, the interface device 114 may be a separate processing unit from the housing 116, so as to allow for remote access/connection thereto. For example, the interface device 114 may be capable of wirelessly connecting (i.e. via wireless LAN, wireless MAN, wireless PAN such as bluetooth or Zigbee, wireless WAN, and the like) to the housing 116 and/or to each individual biologic processing unit 102. In embodiments, the interface device 114 may be a processing unit separate from the housing 116 but still connected to the housing 116 and/or each biologic processing unit 102 via hardwire connection, such as ethernet, fiber optics, and the like. The hardwire connection may allow for semi-flexible location of an end user relative to the housing 116, without necessitating wireless connectivity. In embodiments, multiple automated selection and support systems 100 may be connected to a hardware connection (e.g. wired LAN network) to provide remote access, data collection, and monitoring.

As described herein, suitably the automated selection and support structures are provided such that the biologic processing units are vertically, or substantially vertically, stacked, supported, or otherwise arranged relative to one another. This decreases the footprint of the combination of biologic processing units and allows for maximum use of laboratory, clean room, warehouse or hospital floor space, etc. This vertical orientation is unique to the various support structures described herein, relative to traditional biologic processing units which are traditionally supported in a horizontal manner (i.e., next to each other on the same plane or substantially the same plane).

Figure 2:
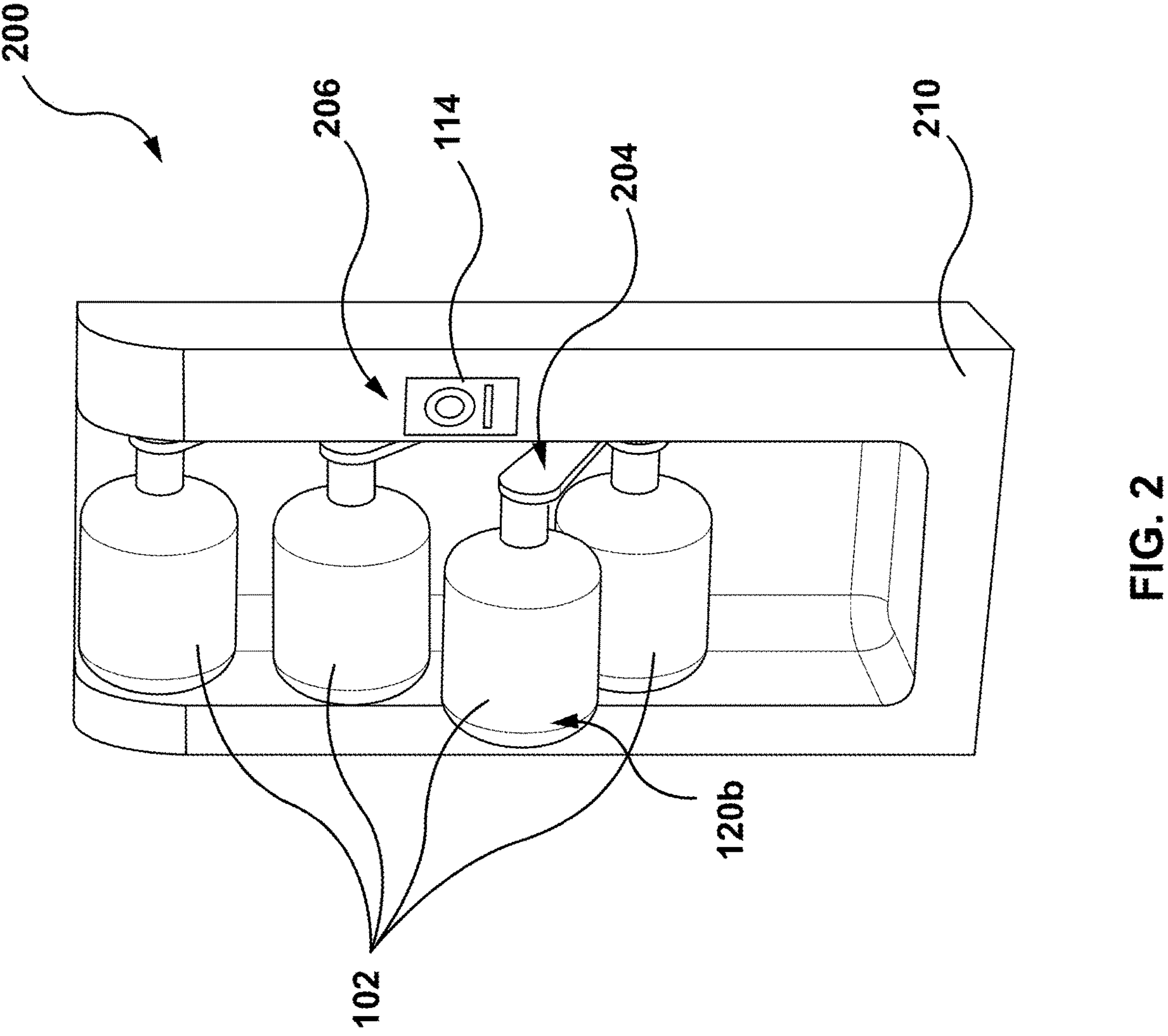
FIG. 2 depicts a perspective view of a second embodiment of an automated selection and support system.
Figure 5:
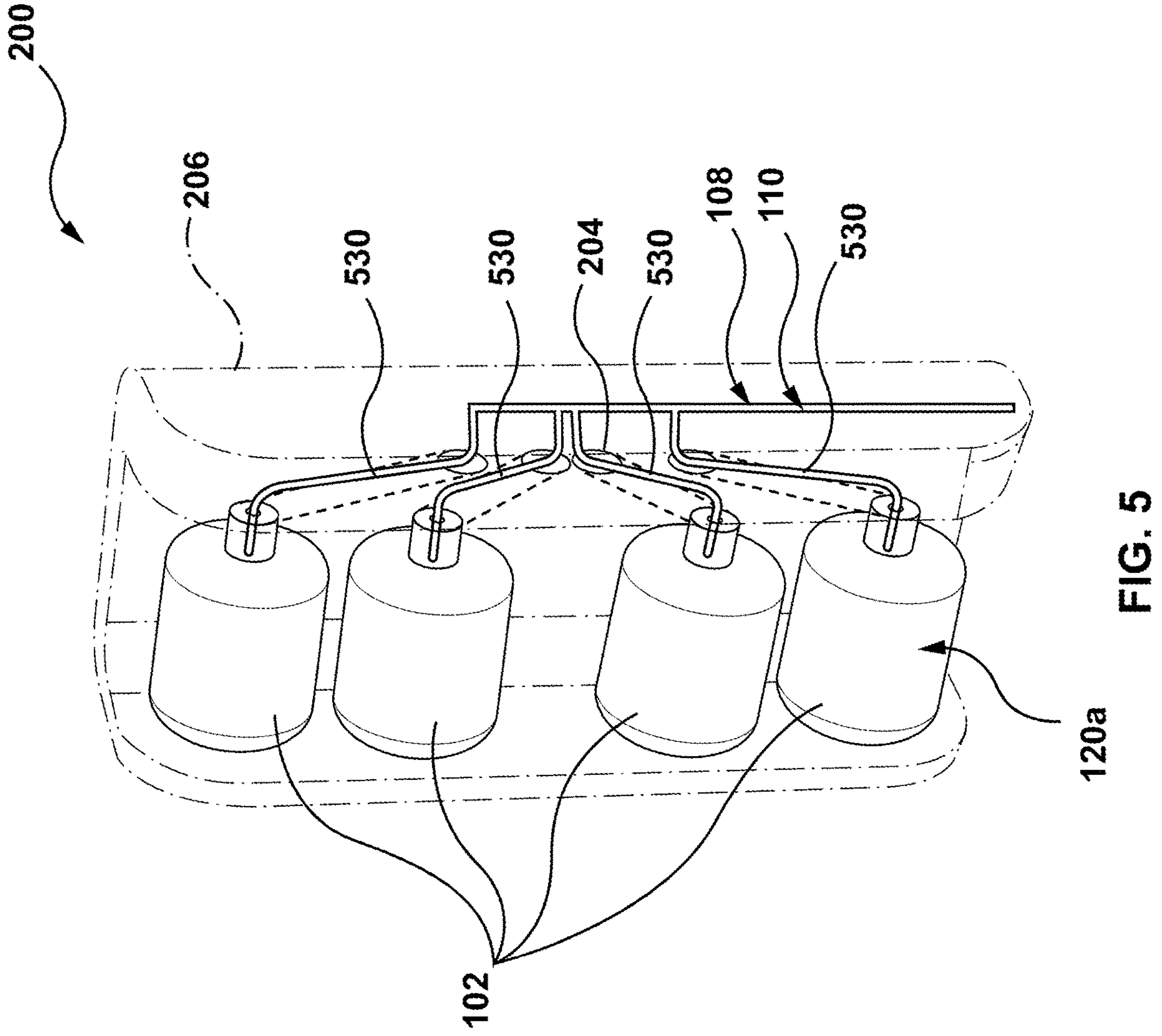
FIG. 5 depicts an alternative internal view of the second embodiment of the automated selection and support system of FIG. 2

FIG. 2 shows a perspective view of an automated selection and support structure 200 using a plurality of swing arms 204. In one exemplary embodiment of the movable support structure 200, a plurality of swing arms 204 having a first end 216 and a second end 218 are used to store and move the biologic processing units 102. The first end 216 of each swing arm 204 is coupled to the housing 206, while the second end 218 is coupled to a single biologic processing unit 102. The swing arms 204 are configured to move each single biologic processing unit 102 between the aforementioned first position 120*a* to the second position 120*b*. In further detail, each swing arm 204 may be configured to rotate about the first end 216 as to move the second end 218 rotationally relative the first end 216. That is, second end 218 moves in an arcing or rotational path, relative to fixed first end 216. In such embodiments, the first position 120*a* may be associated with a specific position of the second end 218 relative to the first end 216. For example and as shown in FIG. 2, the first position 120*a* may be determined as when the second end 218 is substantially vertical relative to the first end 216. Further, the second position 120*b* may be associated with a rotational position wherein the second end 218 is positioned as to be accessible by a user. In some embodiments, the second embodiment is associated with the biologic processing unit 102 being positioned at a height relative to the floor that is accessible to the user. Further, it is envisioned, that the first position 120*a* of each of the biologic processing units 102 are different, as to allow for each biologic processing unit 102 to be stored in the first position 120*a* simultaneously (i.e., in a vertical position relative to the first end 216), as shown in FIG. 5. However, as shown in FIG. 2, in some embodiments, each biologic processing unit 102 can be positioned in the same, second position 120*b*, as to allow only a singular biologic processing unit 102 to be presented to a user at a time. However, configurations are envisioned that allow for multiple biologic processing units 102 to be presented to the user simultaneously.

The swing arms 204 may be of varying dimensions to suit the requirements of supporting each biologic processing unit 102. For example, as shown in FIG. 2, there are four biologic processing units 102 stacked vertically, and, therefore, the top and bottom biologic processing units 102 have longer swing arms 204 in comparison to the two interior biologic processing units 102. Further, the two interior biologic processing units 102 have shorter swing arms 204 that, in some embodiments, have overlapping first ends. This is merely an exemplary configuration, and it is envisioned that the number of biologic processing units 102 supported by each automated selection and support structure 200 may vary. It is envisioned, that by having a single swing arm 204 independently controlling each biologic processing unit 102, that the movement of a singular biologic processing unit 102 does not affect other biologic processing units 102.

In some embodiments, the swing arm 204 may be rotationally limited as to protect the biologic processing units 102 from damage from unintentional movement. In further detail, each swing arm 204 may be restricted only to be able to rotate between the first position 120*a* and the second position 120*b*. For example, a series of hard stops or guards can be positioned as to limit the rotational movement of the swing arm 204. In one embodiment, it is envisioned that the arm may be required to rotate between −100 to +100 degrees (relative to the plane of base 210 or the surface on which housing 206 sits) to transition between the first position 120*a* and the second position 120*b*. Suitably, the first position 120*a* is between about +80 to +100 degrees relative to base 210 or the plane of the surface on which housing 206 sits, and in embodiments, the first position 120*a* is about +90 degrees (i.e., perpendicular) to base 210 or the plane of the surface. In embodiments, the second positions is between about −10 degrees to about +45 degrees relative to base 210 or the plane of the surface on which housing 206 sits. That is, the second position 120*b* is suitably horizontal, including substantially parallel (i.e. 0 degrees relative to base 210 or the plane of the surface on which housing 206 sits), to base 210 or the plane of the surface. In such embodiments, the swing arm 204 itself does not have to be substantially parallel to base 210 or the plane of the surface.

A position guard 429 may be located within the swing arm 204, particularly at the first end 216, or within the housing

206. The position guard 429 allows for the swing arm 204 and the biologic processing unit 102 to be stored at the first position 120*a* without requiring the motor 424 to maintain the swing arm 204 at the first position 120*a*. The position guard 429 may be positioned at the first end 216 as to stop the ability for the swing arm 204 to rotate. In some embodiments, the position guard 429 may be controlled by the interface device 114 and may selectively control when the swing arm 204 may rotate. Further, a second position 120*b* guard may be positioned as to stop the swing arm 204 and the second end 218 once it reaches the second position 120*b* so that the motor 424 is not required to hold the swing arm 204 in the second position 120*b*. It is further envisioned, that in some embodiments, the position guards 429 may be in communication with the interface device 114 of the automated selection and support system 200 as to be automatically and/or selectively engaged and disengaged. Additional position guards 429 may be utilized in the support system 200 to allow for the biologic processing unit 102 to be maintained at any number of desired positions between the first position 120*a* and the second position 120*b*, for example, to carry out certain maintenance requirements, etc.

In some embodiments of the automated selection and support structure 200, four individual swing arms 204 (or 2, or 3, or 4, or 5, or 6, or 6, or 7, or 8, etc.) are connected to the housing 206 and, as shown in FIG. 2, four biologic processing units 102 can be supported by the automated selection and support structure 200. As shown in FIG. 2, the first end 216 of each swing arm 204 is connected at the housing 206 as to allow for each biologic processing unit 102 to move between the first position 120*a* and the second position 120*b* without interfering with the other biologic processing units 102. Each biologic processing unit 102 is configured to move independently of the movement of other biologic processing unit 102, and, further, each swing arm 204 is configured to reduce any forces that may be placed on the other non-moving parts.

Figure 3:
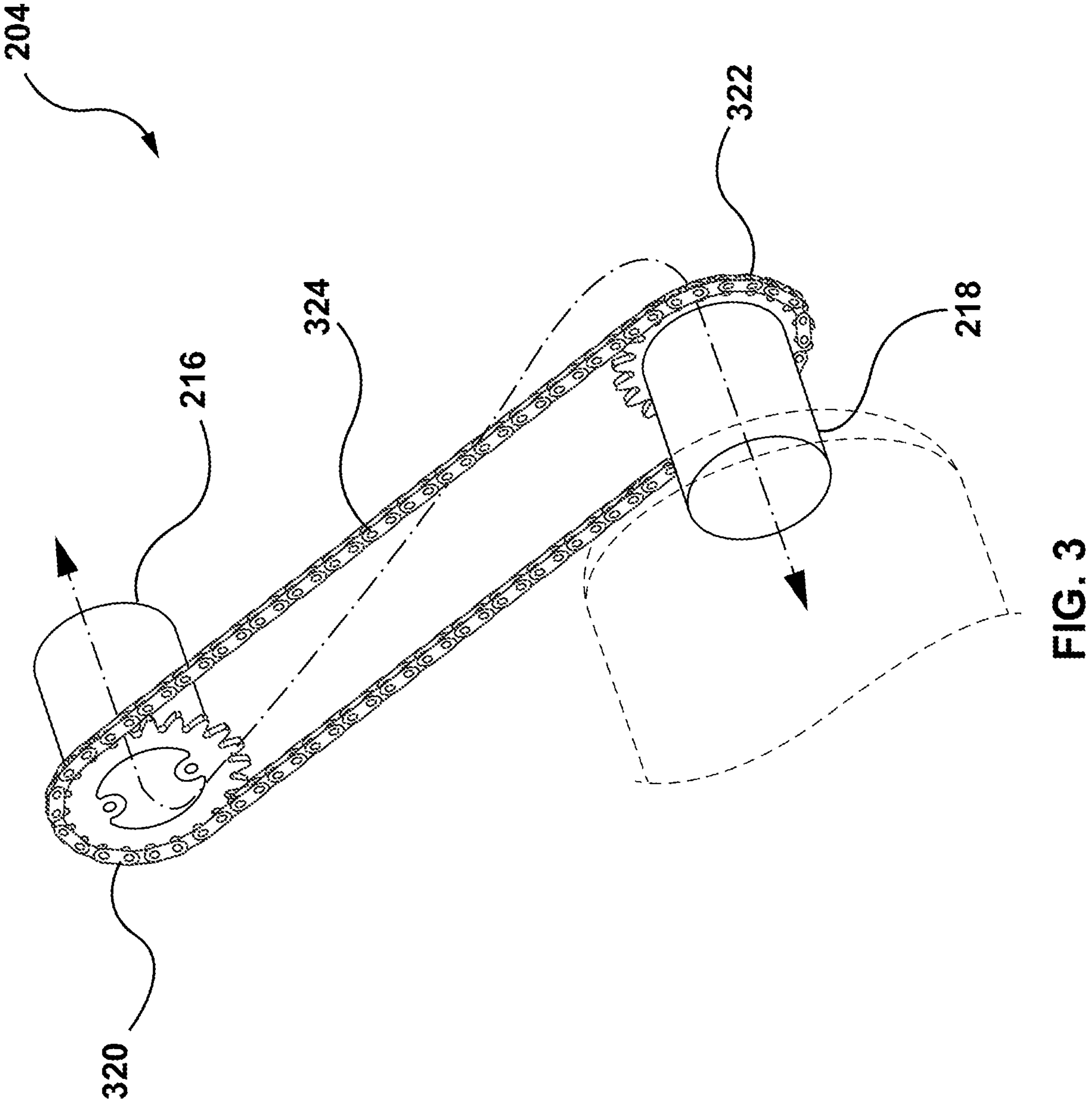
FIG. 3 depicts an internal view of a swing arm of the second embodiment of the automated selection and support system of FIG. 2.

Referring to FIG. 3, which shows an internal view of the swing arm 204, the swing arm includes a first gear 320 affixed to the housing 206 at the first end 216 and a second gear 322 affixed to the biologic processing unit 102 at the second end 218. The first and second gears 320, 322 are coupled by a chain 324 or other connection device (e.g., band or belt), so that when the swing arm 204 rotates about the first end 216 the chain 324 will move as to rotate the second gear 322 as to level the single biologic processing unit 102. Due to the movement of the chain 314, the biologic processing unit 102 is maintained in a level position between the first and second position 120*bs*, i.e., kept rotationally level at the first position 120*a*, the second position 120*b*, and during the transition between the two positions. Suitably, the biologic processing unit 102 is configured to rotate proportionally to the rotation of the swing arm 204 relative to the first end 216, allowing for the biologic processing unit 102 to remain level as the swing arm 204 rotationally displaces the biologic processing unit 102. In some embodiments, by maintaining the biologic processing unit 102 at a consistent level, the rotational and translational forces placed onto the biologic processing unit 102 are reduced or minimized, lowering the overall risk that the biologic processing unit 102, or the processes within, are damaged. This form of leveling system is merely exemplary and other leveling systems known in the art may be used.

Figure 4:
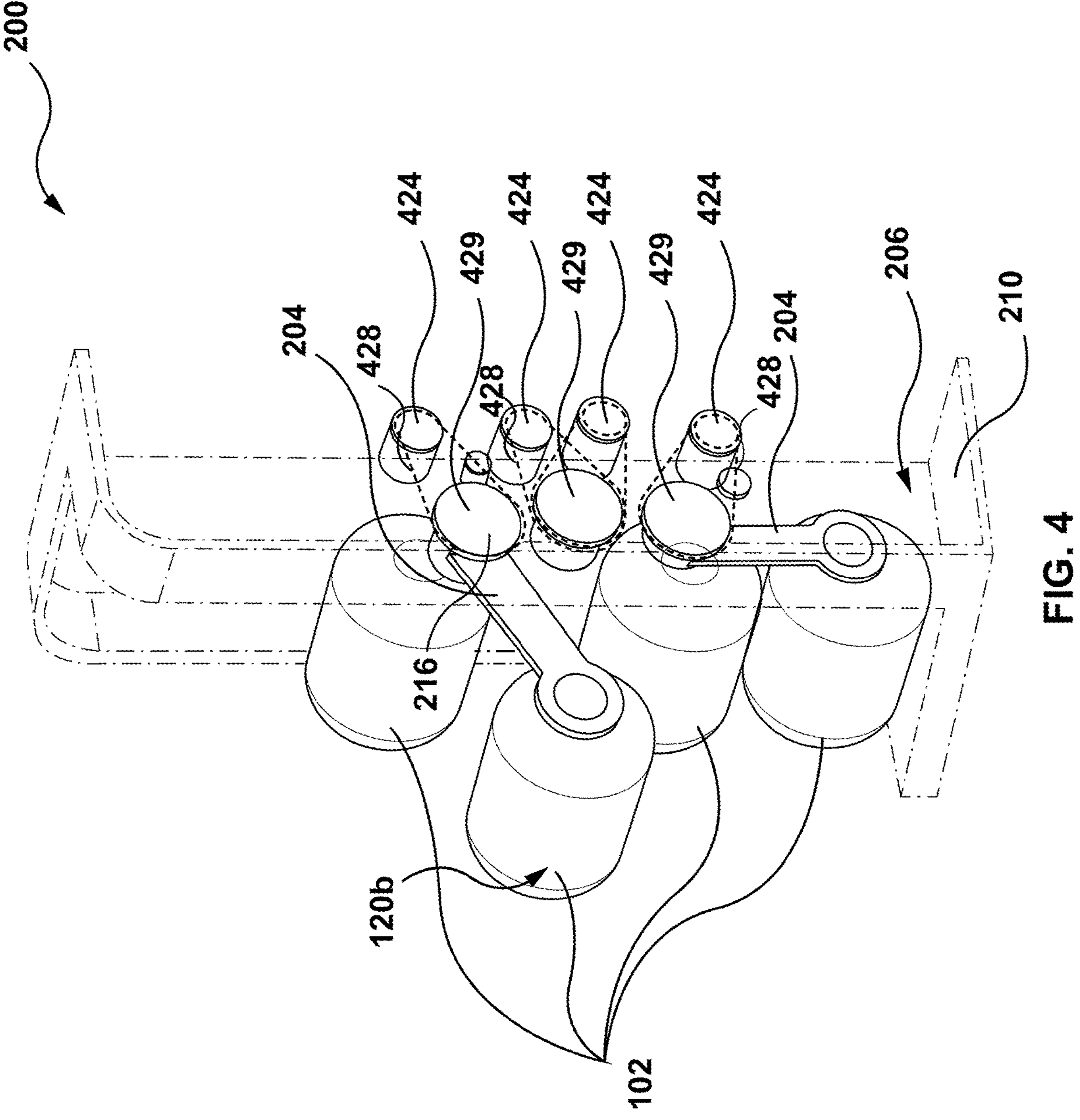
FIG. 4 depicts an internal view of the second embodiment of the automated selection and support system of FIG. 2.

FIG. 4 shows the inside of the housing 206 of an embodiment of the automated selection and support structure 200. The rotation of each of the swing arms 204 is controlled by motors 424 that are operably coupled to the first end 216 of the swing arm 204 by a drive belt 428 (or, in embodiments, a chain, rod, cam, band, or any other viable active control device). In some embodiments, it is envisioned that each swing arm 204 has an independent motor 424 to control the rotation and movement of each swing arm 204. Alternatively, each of the swing arms 204 may be controlled by a singular central motor 424, wherein the motor 424 may selectively engage with each individual swing arm 204. As shown in FIG. 4, the drive belts 428 may be positioned at the rotation point, i.e. the first end 216, of the swing arms 204, which, in some embodiments, results in the drive belts 428 being positioned to overlap with one another.

FIG. 5 shows a schematic view of the housing 206 of the automated selection and support structure 200, wherein a potential layout of the electrical inputs and gas inputs is shown. The electrical system 108 and the gas supply system 110 may be operatively coupled (i.e. connected to allow for electric power, control, data transfer, and gas supply and return) to each of the processing units 102 through a series of conduits 530 that are positioned within the housing 106 and, in some embodiments, the conduits 530 extend from the first end 216 of each of the swing arms 204, through the swing arm 204, and connecting to the biologic processing unit 102 at the second end 218 of the swing arms 204. Further, it is envisioned that the electrical system 108 and the gas supply system 110 may be positioned within the housing 206.

The housing 206 may contain all components required for the moveable support structure 204 to transition the automated biologic processing units 102 as well as contain any resources necessary for the automated biologic processing units 102 to function properly. For example, the housing 206 may contain the mechanical components and electrical components necessary to operate numerous moveable support structures 204, such as motors, pulleys, processors, electrical wires, etc. Further, an interface device 114 may be positioned at or on the housing 206, allowing for a user to interact with the systems of the automated selection and support system 200. The housing 206 may incorporate the interface device 114 into the housing, as to present the user with information regarding the automated biologic processing units 102 and the systems of the automated selection and support system 200. The housing 206 is configured to allow for a user to access the interior systems and components housed by the housing 206.

In operation, a user may interact with the interface device 114 (e.g., computer, tablet, mobile device, etc.) as to select an automated biologic processing unit 102. The interface device 114 will then engage the motor 424 that is associated with the specified automated biologic processing unit 102. The motor 424, via the belt drive 428, will begin to rotate the second end 218 and first gear 320, rotating the swing arm 204. Once the swing arm 204 is placed in the second position 120*b*, the user may interact with the biologic processing unit 102. When the user has completed interacting with the biologic processing unit 102, the user may interact with the interface device 114 to return the swing arm 204 to the first position 120*a*. The configuration shown in FIG. 2-5 independently moves each automated biologic processing unit 102 such that any movement failure or errors within the automated support and selection structure 200 will not result in the failure or damage to of each of the other automated biologic processing units 102.

A heat management system 112 may be positioned either internally or externally in relation to the automated support and selection structure 200, wherein the heat management system 112 is configured to keep each of the automated biologic processing units 102 at a relatively consistent temperature (e.g. ±5° C.). As stated above, the automated biologic processing units 102 require a consistent temperature in order to operate properly. It is envisioned that each automated biologic processing unit 102 may produce heat, and, in some embodiments, the heat management system 112 may be used to remove any heat from each of the automated biologic processing units 102. As stated above, the heat management system 112 may be housed in each of the automated selection and support systems 100 or may be positioned externally relative to the automated biologic processing units 102. For example, multiple automated selection and support systems 100 may be positioned in a temperature-controlled room, wherein the heat management system 112 may be configured to control the temperature of the room or provide live data regarding the temperature of the units 102 to an external ventilation system. When positioned internally, the ventilation systems 112 may use a plurality of fans to either push or pull ambient air across the surface of each of the automated biologic processing units 102. The ambient air may then be regurgitated back into the surrounding ambient air or may be cooled by an internal or external temperature interface device, such as an air conditioner. Heat management system 112 can also comprise a fluid cooled system in which tubing or similar structures run on or near the surface of the automated biologic processing units 102, or can run within the units, to cool the units. Further, the heat management system 112, if positioned internally or externally, may be controlled or in communication with a central computer system or by an independent computer system specifically configured for the heat management system 112. Further, it is envisioned that the temperature of each of the biologic processing units 102 will be monitored as to provide the user and the computer system with information as to whether the biologic processing units 102 is falling out of a range of acceptable temperature and to make any necessary corrections to return the biologic processing units 102 to an acceptable temperature range.

Figures 6, 7:
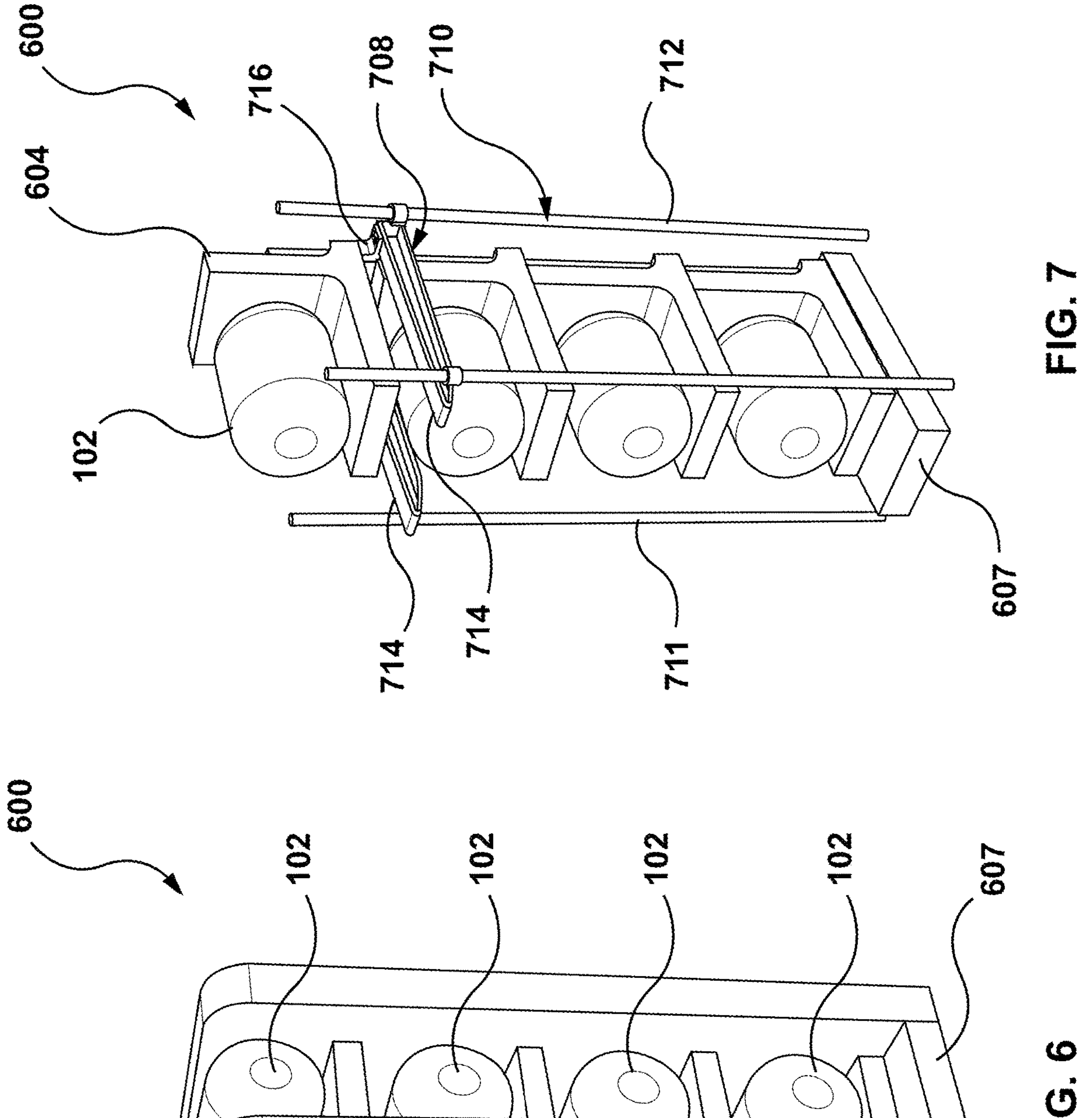
FIG. 6 depicts a third embodiment of an automated selection and support system.
FIG. 7 depicts an internal view of the third embodiment of the automated selection and support system of FIG. 6.

In an alternative embodiment of an automated selection and support system 600, as shown in FIG. 6, the automated selection and support system 600 is configured to support a plurality of automated biologic processing units 102 that may be positioned in either a first position 120*a* for storage or a second position 120*b* for presenting the automated biologic processing unit 102 to a user. The system 600 includes a plurality of holding shelves 604, a housing 606, and a movable gantry 708, wherein each of the plurality of holding shelves 604 are configured to hold and couple one of the plurality of automated biologic processing units 102. Further, the movable gantry 708 is able to selectively couple each of the holding shelves 604, wherein the movable gantry 708 is configured to move the selected holding shelves 604 between the first position 120*a* and the second position 120*b*.

In further detail, each holding shelves 604 is configured to support one of the automated biologic processing units 102 and is shown in FIG. 7, wherein the automated selection and support system 600 is shown with the housing 606 removed. Each holding shelf 604 couples to the automated biologic processing unit 102 either at the base of the automated biologic processing unit 102 or at one end of the automated biologic processing unit 102, in particularly at the back end of the automated biologic processing unit 102. The coupling point of each holding shelf 604 provides the biologic processing units 102 with electricity, gas, and, in some embodiments, ventilation. To be more specific, the coupling point of the holding shelf 604 may have, in addition to a coupling mechanism, an opening that provides the biologic processing units 102 with access to the resources required to operate properly.

The moveable gantry 708 is shown in FIG. 7 and is configured to move vertically between the plurality of holding shelves 604 and is capable of selectively coupling to each of the plurality of holding shelves 604 as to selectively transition the automated biologic processing units 102 between the first position 120*a* and the second position 120*b*. The moveable gantry 708 is positioned on a series of rails 710 that extend vertically from the base 607 of the housing 606 to the top holding shelf 604. The moveable gantry 708 is configured to be operably coupled to the series of rails 710 as to selectively travel vertically up and down the series of rails 710. Further, the gantry 708 has a pair of horizontal sliders 714, wherein each horizontal slider 714 has a first end and a second end which are operably coupled to a front rail 711 and a back rail 712. As shown in FIG. 7, the gantry 708 is operably coupled at the four corners of the pair of horizontal sliders 714.

In operation, a user may interact with the interface device 114 (e.g., computer, tablet, mobile device, etc.) as to select an automated biologic processing unit 102. The interface device 114 will control the movement and speed of the moveable gantry 708 and the horizontal sliders 714 to transition the biologic processing unit 102 from the first position 120*a* to the second position 120*b*. As stated above, the interface device 114 allows for the user to monitor the status of each of the automated biologic processing units 102 and, in some embodiments. When the user has completed interacting with the automated biologic processing unit 102, the user may again interact with the interface device 114 to return the automated biologic processing unit 102 back to the first position 120*a* (e.g., for storage and maintenance).

Figure 8:
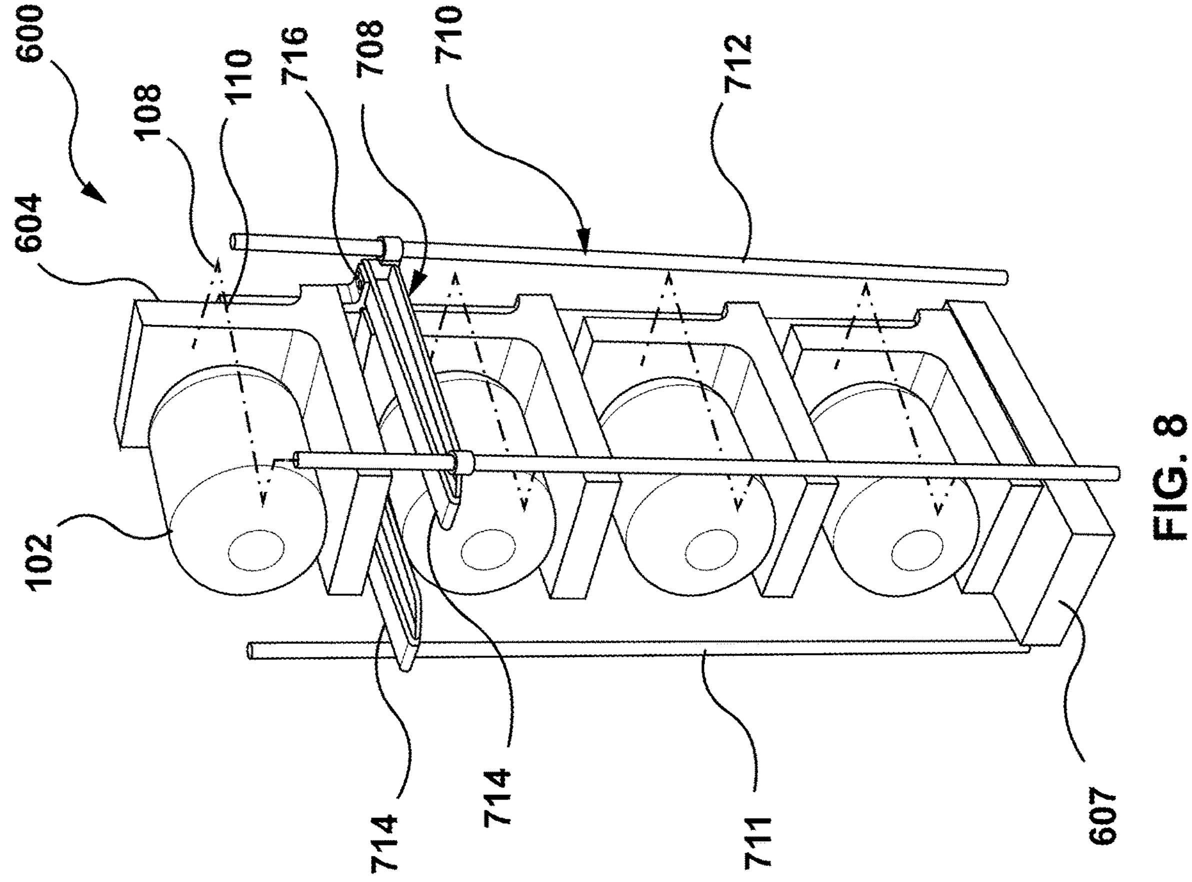
FIG. 8 depicts an alternative internal view of the third embodiment of the automated selection and support system of FIG. 6.
Figure 9:
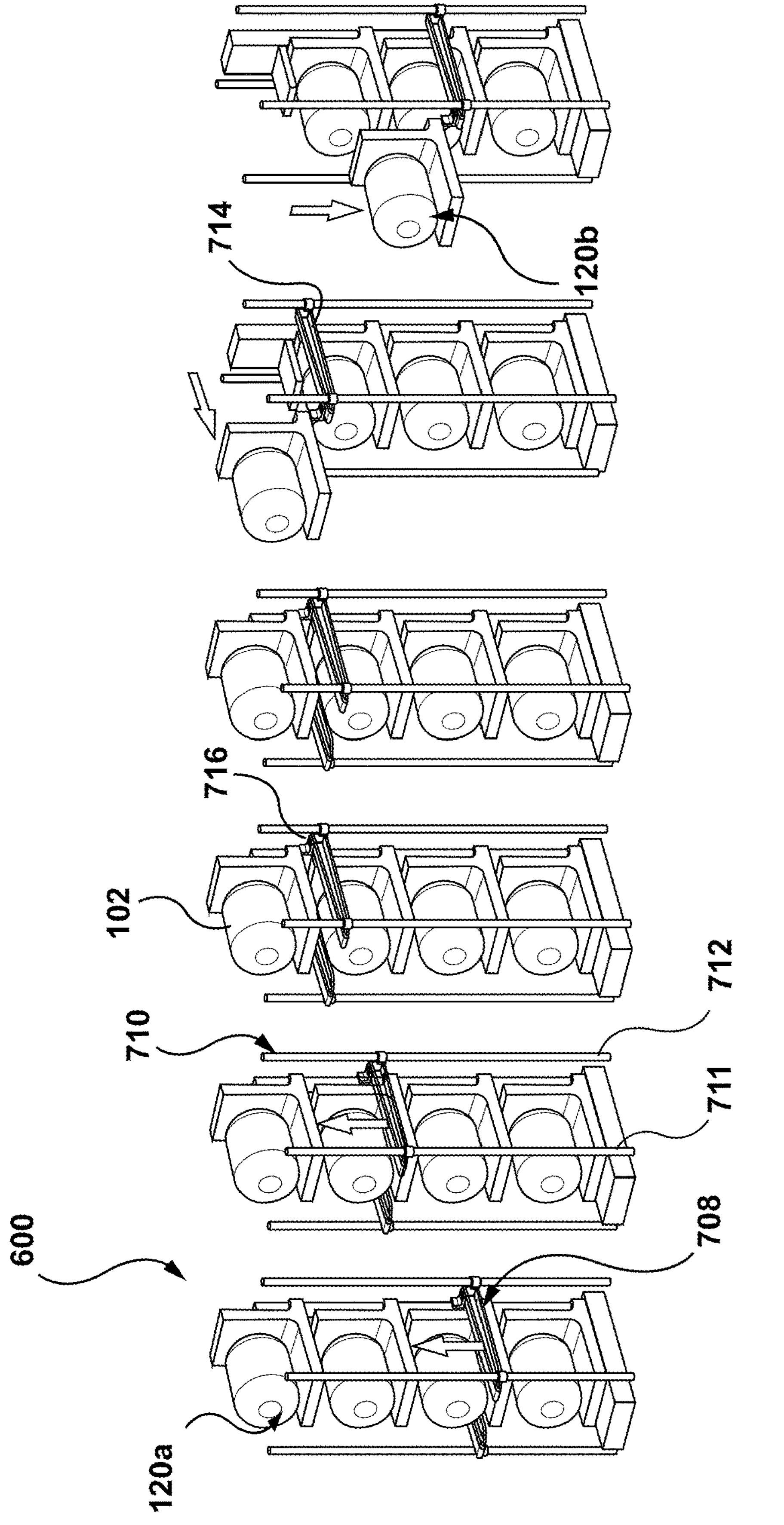
FIG. 9 depicts the third embodiment of the automated selection and support system of FIG. 6 moving an automated biologic processing unit between a first position and a second position.

The horizontal sliders 714 are configured to travel up and down vertically with the movable gantry 708, wherein the horizontal sliders 714 have a clip or attachment structure 716 that is compatible with gripping or coupling to each holding shelf 604 as shown in FIG. 8. Once the attachment structure 716 grips the holding shelf 604, the horizontal sliders 714 will move the holding shelf 604 and, subsequently, the automated biologic processing unit 102 horizontally forward, as seen in FIG. 9. The gantry 708 will then move vertically to a position that will present the holding shelf 604 and the automated biologic processing unit 102 to the user (i.e., the last position). Various motors and gears are to be utilized in the movement of the movable gantry 708 and the horizontal sliders 714.

As shown in FIG. 6, the housing 606 encompasses the moveable gantry 708, the horizontal sliders 714, and any systems required to support the automatic biologic processing units 102. The housing 606 includes a base 607 that is located at the bottom of the housing 606. The position of the housing 606 allows for the moveable gantry 708 and the horizontal sliders 714 to be completely encompassed by the housing 606. Further, the holding shelves 604 may be positioned completed outside of the housing 606, as to allow for the holding shelves 604 to move horizontally relative to the housing 606.

As shown in FIG. 8, housing 606 (removed in FIG. 8 to assist with viewing), suitably includes the electrical system 108 and the gas supply system 110 operatively coupled (i.e. connected to allow for electric power, control, data transfer, and gas supply and return) to each of the processing units 102 through a series of conduits or other similar structures. As illustrated, in embodiments, one or more of the electrical system 108 and the gas supply system 110 can travel up, including within, one or more of the rails 710. As shown, each processing unit 102 is fed by its own electrical system 108 and gas supply system 110, so that appropriate changes can be made to the electricity and/or gas provided to individual processing units 102 as desired or required.

As described herein, the heat management system 112 for the automated selection and support system 600 may be positioned either internally or externally in relation to the automated support and selection structure 600, wherein the heat management system 112 is configured to keep each of the automated biologic processing units 102 at a relatively consistent temperature (e.g. ±5° C.). As stated above, the automated biologic processing units 102 require a consistent temperature in order to operate properly. It is envisioned that each automated biologic processing unit 102 may produce heat, and, in some embodiments, the heat management system 112 may be used to remove any heat from the surface of each of the automated biologic processing units 102. As stated above, the heat management system 112 may be placed in the housing 606 of the of each of the automated selection and support system 600 or may be positioned externally. For example, multiple automated selection and support systems 600 may be positioned in a temperature-controlled room, wherein the heat management system 112 may be configured to temperature of the room or provide live data regarding the temperature of the units 102 to an external ventilation system. When positioned internally, the ventilation systems 112 may us a plurality of fans to either push or pull ambient air across the surface of each of the automated biologic processing units 102, or a fluid-cooled system, as described herein, may be used.

The process of moving one of the plurality of biologic processing units 102 using automated selection and support system 600 between the first position 120*a* and the second position 120*b* is shown in FIG. 9. In order to move the biologic processing unit 102, the user may first select one of the plurality of automated biologic processing units 102 via the interface device 114. As stated above, the horizontal sliders 714 are each associated with a holding shelf 604. The moveable gantry 708 will then vertically move up and down the series of rails 710 until the moveable gantry 708 reaches the vertical position of the biologic processing unit 102. Once the moveable gantry 708 has been positioned at the selected the automated biologic processing unit 102, the horizontal sliders 714 will then be positioned at the holding shelf 604, allowing for the attachment structures or clips 716 to engage with and couple to the holding shelf 604. The horizontal sliders 714 of the moveable gantry 708, will then slide the holding shelf 604, as shown in FIG. 9, out away from the other holding shelfs. Once the holding shelf 604, and subsequently the biologic processing unit 102, is moved horizontally, the moveable gantry 708 will then move the selected holding shelf 604 vertically (either up or down) into a position (the second position 120*b*) where the biologic processing unit 102 is accessible by a user.

Once the user has completed using the automated biologic processing unit 102, the moveable gantry 708 may move vertically as to return the holding shelf 604 to the first position 120*a*. The horizontal sliders 714 may then horizontally move the holding shelf 604 and the automated biologic processing unit 102 back to the first position 120*a*. The moveable gantry 708 may then disconnect from the holding shelf 604, allowing for user to access another biologic processing unit 102.

Figures 10, 11:
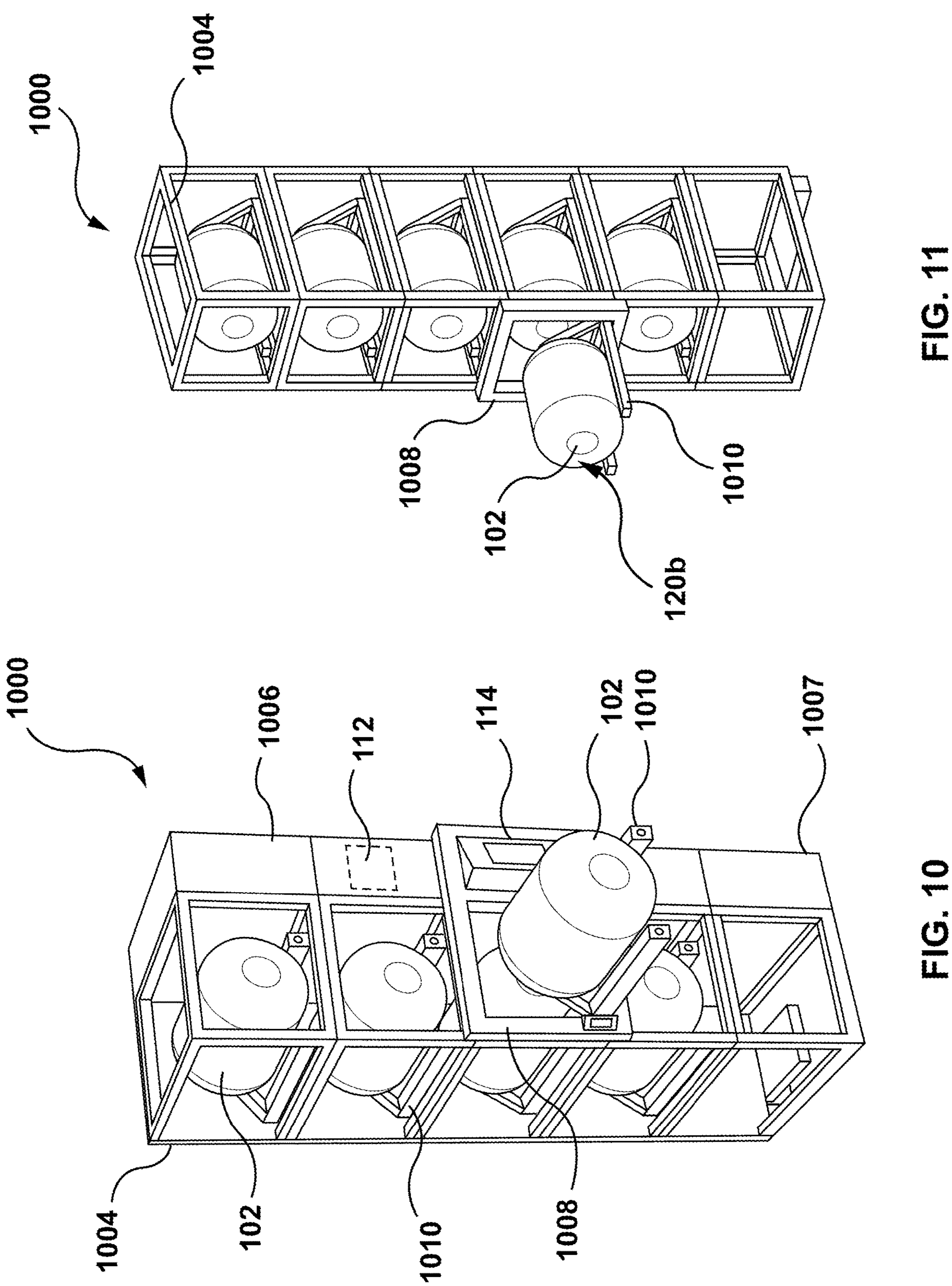
FIG. 10 depicts a perspective view of a fourth embodiment of an automated selection and support system.
FIG. 11 depicts an internal view of the fourth embodiment of the automated selection and support system of FIG. 10.

An additional embodiment of the automated selection and support structure 1000 is shown in FIG. 10. The automated selection and support system 1000 is configured to support the plurality of automated biologic processing units 102, wherein the structure 1000 is capable of positioning the automated biologic processing unit 102 either in a first position 120*a* for storage and maintenance or in a second position 120*b* for presenting the automated biologic processing unit 102 to the user. The structure 1000 generally includes a plurality of vertically stacked modular holding cells 1004, a housing 1006, a shuttle 1008, and a plurality of chassis 1010. Each of the holding cells 1004 has one of the plurality of chassis 1010 positioned within, wherein each of the chassis 1010 is configured to support and secure one of the plurality of automated biologic processing units 102.

In further detail and as shown in FIG. 11, each holding cell 1004 is sized to fit both one of the plurality of chassis 1010 and one of the plurality of automated biologic processing units 102. The embodiment shown in FIG. 11 has the plurality of holding cells 1004 being stacked vertically on top of one another, with each holding cell 1004 being configured to be an open-cell. In further detail, the open sides of each of the cells 1004 allows for air flow to more readily transfer across each of the automated biologic process units 102. The exemplary system 1000 shows five holding cells 1004 stacked vertically, however, this is merely exemplary, and a number of alternative configurations are envisioned.

One of the plurality of chassis 1010 is positioned within each of the holding cells 1004, wherein each chassis 1010 is configured to move both the chassis 1010 and the automated biologic processing unit 102 out of the interior of the holding cell 1004. The chassis 1010 may connect the automated biologic processing unit 102 to the housing 1006 as to provide each of the automated biologic processing units 102 the necessary resources (i.e. gas, electricity) in order to operate and successfully complete their intended functions.

The moveable shuttle 1008 is configured to move vertically across the surface of the holding cells 1004 as to selectively couple, and, subsequently, move the automated biologic processing units 102 from the first position 120*a* to the second position 120*b*. The moveable shuttle 1008 may selectively couple to each of the chassis 1010 using a series of motors and gears. Once the moveable shuttle 1008 is coupled to the chassis 1010, the shuttle 1008 may move the chassis 1010, and subsequently, the automated biologic processing unit 102, horizontally out of the cells, allowing for the moveable shuttle 1008 to vertically move the chassis 1010 and the automated biologic process units 102 vertically to present them to the user.

In operation, the user may interact with the interface device 114 (e.g., computer, tablet, mobile device, etc.) as to select one the plurality of automated biologic processing units 102. The interface device 114 will control the movement and speed of the shuttle 1008, as well the coupling and movement of the chassis 1010. As previously stated, the interface device 114 allows for the user to monitor the status of each of the automated biologic processing units 102. When the user has completed interacting with the automated biologic processing unit 102, the user may again interact with the interface device 114 to return the automated biologic processing unit 102 back to the first position 120*a*. As shown in FIG. 10, the interface device 114 is positioned on the shuttle 1008, however, this is merely exemplary, and the interface device may be placed on either portion of the automated selection and support structure 1000 or may be placed remotely to the automated selection and support system 100.

Figure 12:
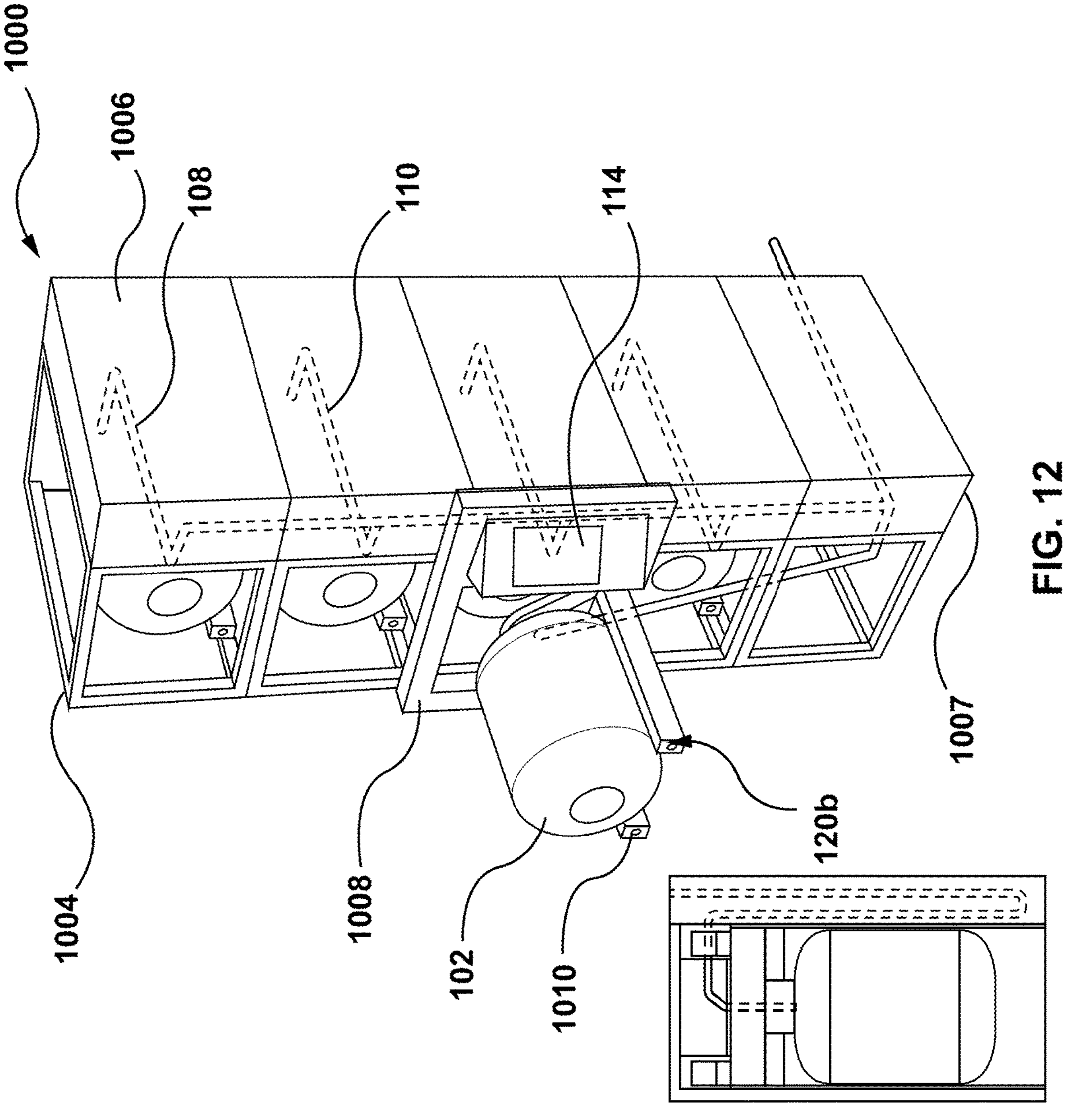
FIG. 12 depicts an alternative internal view of the fourth embodiment of the automated selection and support system of FIG. 10.

As shown in FIG. 12, the housing 1006 encompasses the mechanics required to move the shuttle 1008, the electronic system, the gas supply, and any ventilation or heat management components that may be necessary. The housing 1006 includes a base 1007 that is located at the bottom of the housing 1006. As shown in FIG. 12, housing 1006, suitably includes the electrical system 108 and the gas supply system 110 operatively coupled (i.e. connected to allow for electric power, control, data transfer, and gas supply and return) to each of the processing units 102 through a series of conduits or other similar structures. As shown, each processing unit 102 is fed by its own electrical system 108 and gas supply system 110, so that appropriate changes can be made to the electricity and/or gas provided to individual processing units 102 as desired or required. When shuttle 1008 selects a particular chassis 1010 to move processing unit 102 from a first position 120*a* to a second position 120*b*, the accompanying electrical system 108 and gas supply system 110 also move accordingly with the shuttle 1008.

Similarly to what was described above, the heat management system 112 for the automated selection and support system 1000 may be positioned either internally or externally in relation to the automated support and selection structure 1000, wherein the heat management system 112 is configured to keep each of the automated biologic processing units 102 at a relatively consistent temperature (e.g. ±5° C.). As stated above, the automated biologic processing units 102 require a consistent temperature in order to operate properly. It is envisioned that each automated biologic processing unit 102 may produce heat, and, in some embodiments, the heat management system 112 may be used to remove any heat from each of the automated biologic processing units 102. As stated above, the heat management system 112 may be placed in the housing 1006 of the of each of the automated selection and support system 1000 or may be positioned externally. For example, multiple automated selection and support systems 1000 may be positioned in a temperature-controlled room, wherein the heat management system 112 may be configured to temperature of the room or provide live data regarding the temperature of the units 102 to an external ventilation system. When positioned internally, the ventilation systems 112 may us a plurality of fans to either push or pull ambient air across the surface of each of the automated biologic processing units 102, or a fluid-cooled system, as described herein, may be used.

Figure 13:
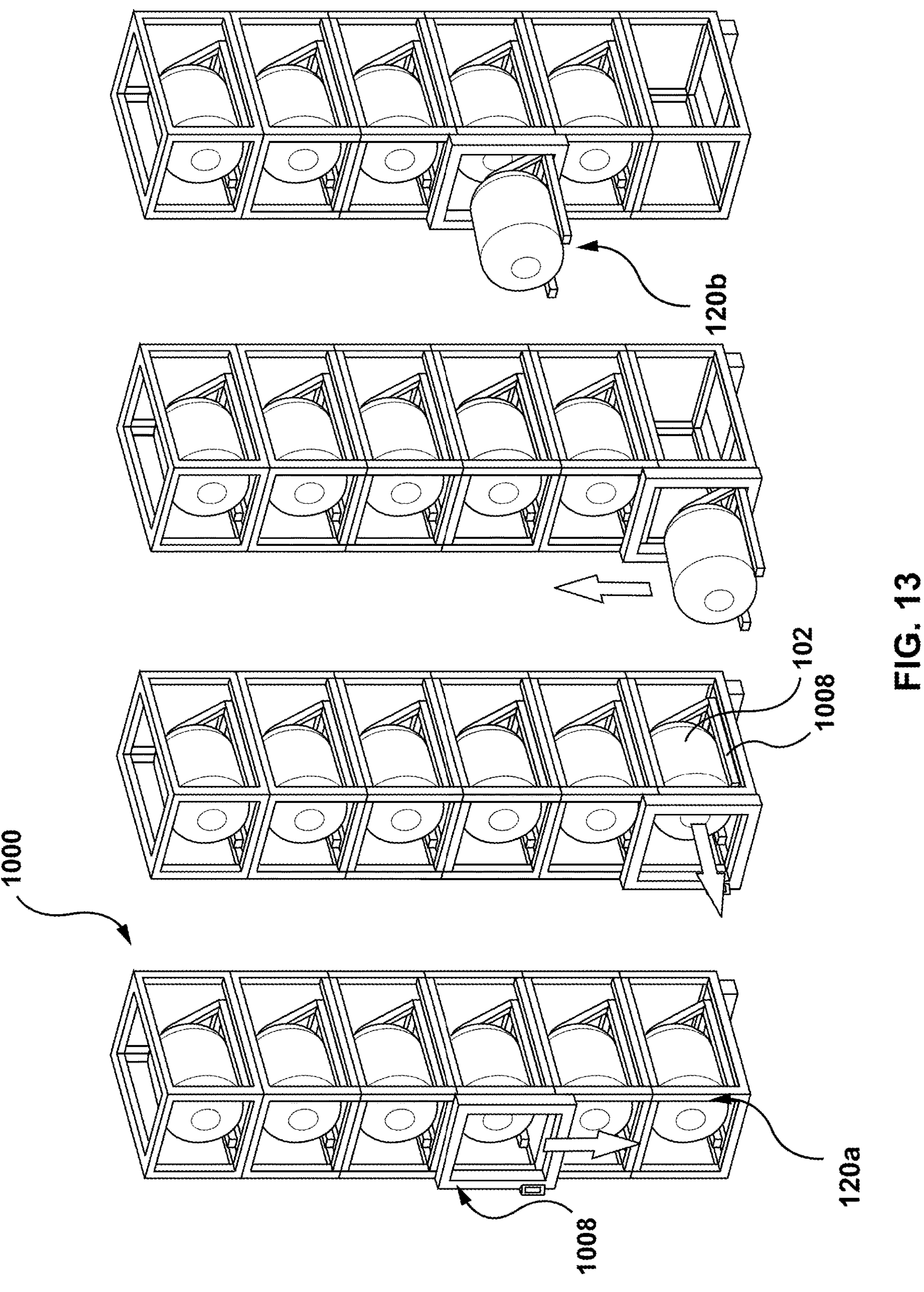
FIG. 13 depicts the fourth embodiment of the automated selection and support system of FIG. 10 moving an automated biologic processing unit between a first position and a second position.

The process of moving the biologic processing unit 102 between the first position 120*a* and the second position 120*b* using the automated selection system 1000 is shown in FIG. 13. In order to move the biologic processing unit 102, the user may first select one of the plurality of automated biologic processing units 102 via the interface device 114. As stated above, once a specific automated biologic processing unit 102 has been selected, the shuttle 1008 will navigate to the holding cell 1004 associated with the selected automated biologic processing unit. The shuttle 1008 will couple to the chassis 1010 that is positioned within the holding cell 1004. The shuttle 1008 will then remove both the chassis 1010 and, subsequently, the automated biologic processing unit 102 from the selected holding cell 1004 by sliding from the holding cell 1004, and, once removed, the shuttle 1008 will move vertically up or down across the plurality of holding cells 1004, until the automated biologic processing unit 102 arrives at the second position 120*b*. The biologic processing unit 102 may then be accessed by a user.

Once the user has completed using the automated biologic processing unit 102, the shuttle 1008 may move across the series of holding cells 1004 as to return the chassis 1010 and the automated biologic processing unit 102 to the original holding cell 1004. The shuttle 1008 may then return the chassis 1010 and the automated biologic processing unit 102 back to the original holding cell 1004 before the shuttle 1008 disconnects from the chassis 1010. The shuttle 1008 is then free again to allow the user to access another biologic processing unit 102.

Figure 14:
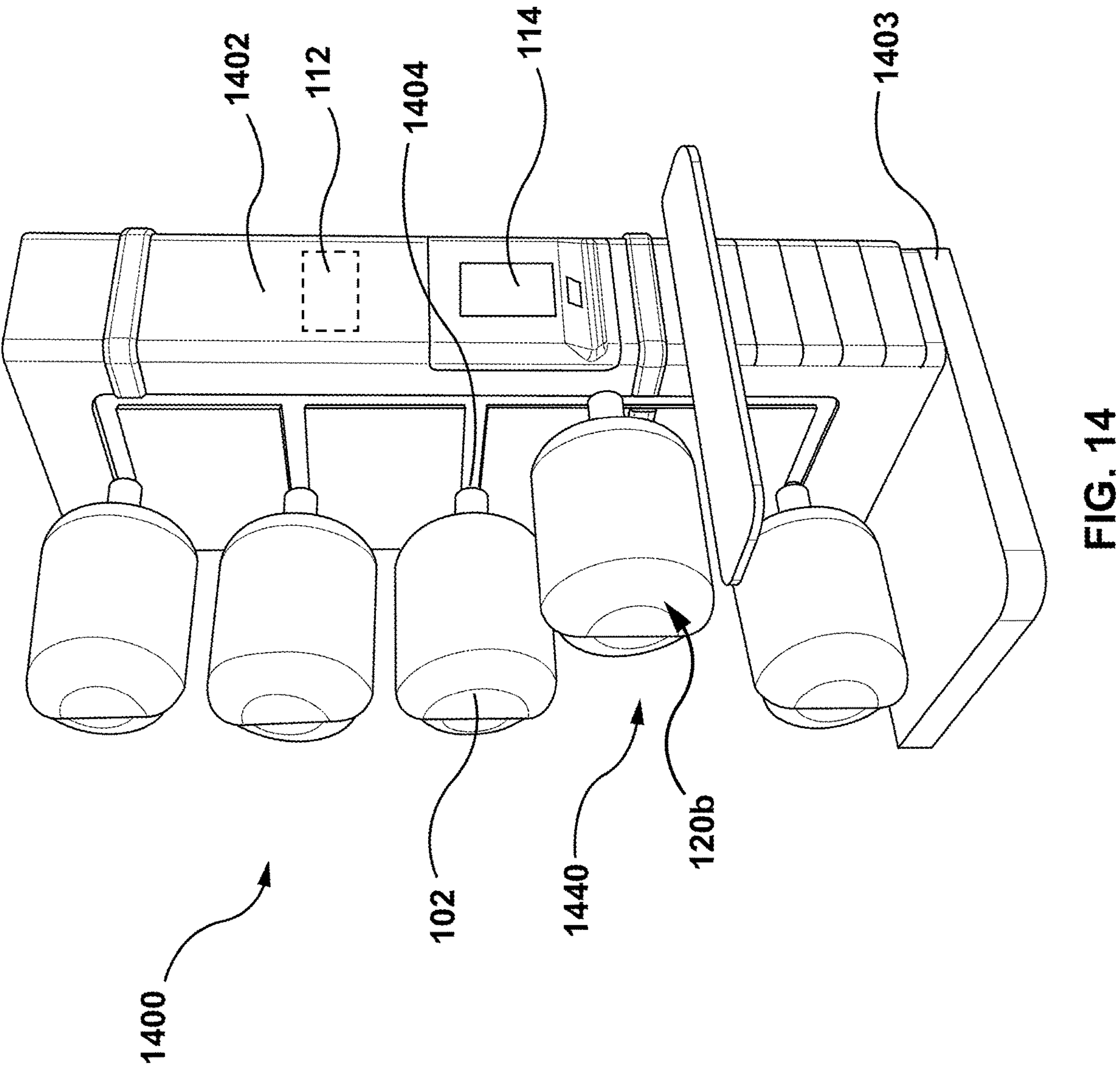
FIG. 14 depicts a perspective view of a fifth embodiment of an automated selection and support system.
Figure 15:
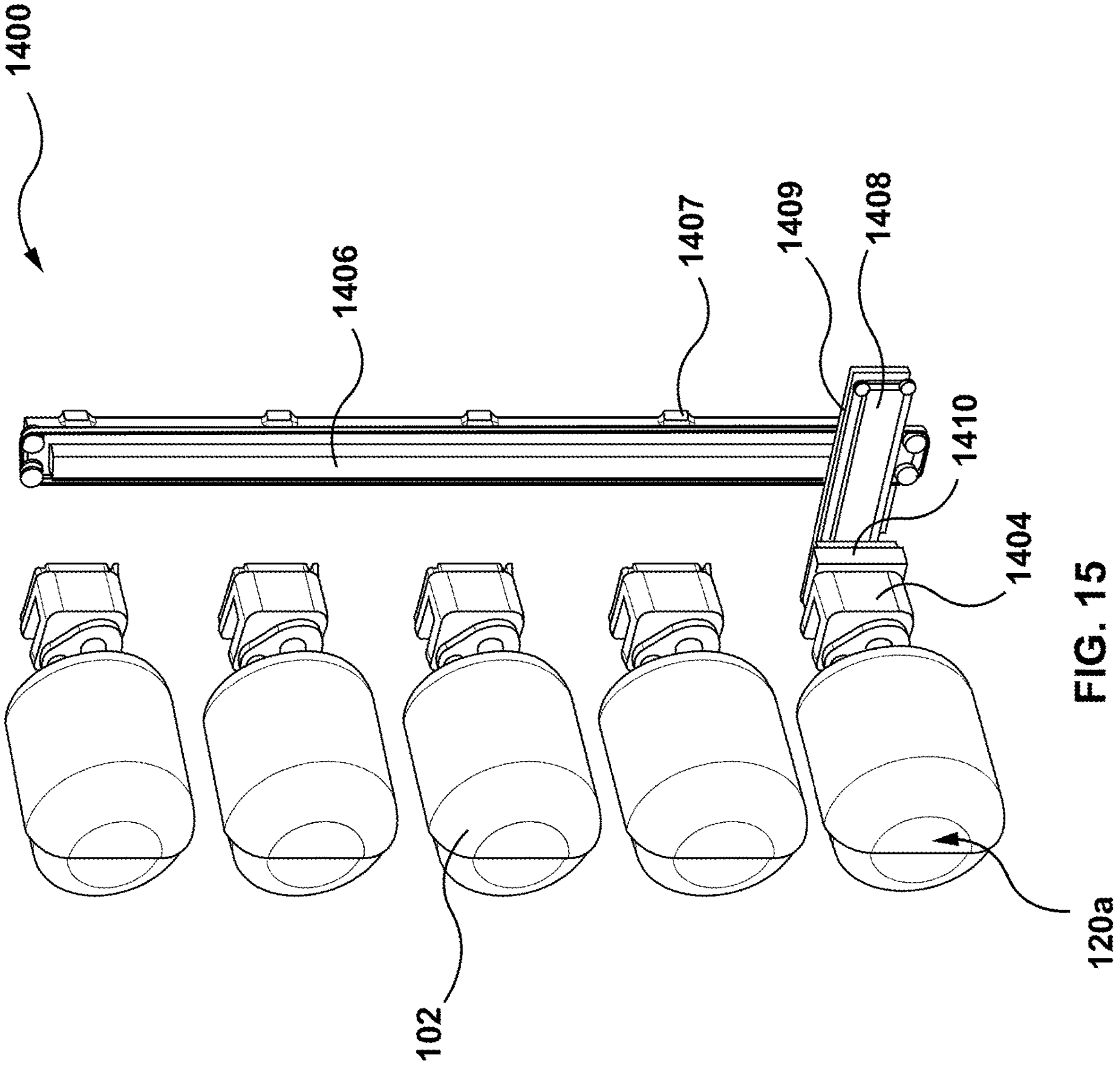
FIG. 15 depicts an internal perspective view of the fifth embodiment of an automated selection and support system of FIG. 14.

An additional embodiment of the automated selection and support structure 1400 is shown in FIGS. 14-15. The automated selection and support structure 1400 is configured to support the plurality of automated biologic processing units 102, wherein the structure 1400 is capable of positioning each of the plurality of automated biologic processing units 102 either in a first position 120*a* for storage and maintenance or in a second position 120*b* presenting the automated biologic processing unit 102 to the user. The automated selection and support structure 1400 includes a housing 1402, a plurality of transfer blocks 1404, a first track 1406, a second track 1408, and a coupler 1410. Each of the transfer blocks 1404 is positioned at and coupled to one of the automated biologic processing units 102, wherein each block 1404 is configured to selectively mate with the coupler 1410. In operation, the user will select one of the plurality of automated biologic processing units 102 and the coupler 1410 will be navigated using the first track 1406 and the second track 1408 to the position of the transfer block 1404 of the chosen automated biologic processing unit 102. Once positioned, the coupler 1410 mates with the transfer block 1404 associated with the selected automated biologic processing unit 102. The automated biologic processing unit 102 is then transitioned from the first position 120*a* to the second position 120*b* using the first track 1406 and the second track 1408. Each biologic processing unit 102 may operate and be translated between the first position 120*a* and the second position 120*b* independently, allowing for optimization of space utilization while simultaneously maintaining usability of the biologic processing units 102.

One transfer block 1404 of the plurality of transfer blocks 1404 is positioned at each of the automated biologic processing units 102. As shown in FIG. 15, each transfer block 1404 is positioned internally relative to a housing 1402 of the automated biologic processing unit 102 (not shown in FIG. 15), while each automated biologic processing unit 102 is positioned externally relative to the housing 1402. The automated biologic processing units 102 may be attached and detached to each of the transfer blocks 1404 as to allow for each of the automated biologic processing units 102 to be removed from the automated selection and support structure 1400 (e.g., for cleaning, sterilization, repair, etc.). Further, each of the transfer blocks 1404 is configured to selectively mate with the coupler 1410 so as to move both the transfer block 1404 and the selected automated biologic processing unit 102 from one position within automated selection and support structure 1400 to a further position, for example the first position 120*a* and the second position 120*b*.

As shown in FIG. 15, the first track 1406 includes a belt 1407 surrounding the perimeter of the first track 1406, the belt 1407 being configured to move the second track 1408. In embodiments, the second track 1408 may be moved by structures other than the belt 1407, such as a chain, rope, band, pulley, ball screw, roller screw, ACME screw, etc. The second track 1408 is coupled to a portion of the belt 1407, so that as the belt 1407 is rotated around the perimeter of the first track 1406, the position of the second track 1408 relative to the first track 1406 may be controlled. Belt 1407 can include any suitable mechanism, including a pully system, gear system, drive belt, band, spoked wheels and corresponding chain, ball screw, roller screw, ACME screw, etc., to allow for movement of first track 1406 and second track 1408. In one exemplary embodiment, and as shown in FIG. 15, the belt 1407 of the first track 1406 is used to control the height or vertical position of the second track 1408 when moved along first track 1406. Similarly, the second track 1408 includes a belt 1409 that surrounds the perimeter of the second track 1408. The coupler 1410 is coupled to the belt 1409 of the second track, so that as the belt 1409 is rotated around the perimeter of the second track 1408 the position of the coupler 1410 is controlled. In the exemplary embodiment set forth in FIG. 15, the belt 1409 controls the horizontal position of the coupler 1410. Therefore, the combination of the first track 1406 and the second track 1408 control both the vertical and the horizontal position of the coupler 1410, and thus the vertical and horizontal movement of biologic processing unit 102 within the support structure 1400. The configuration shown in FIGS. 14-17 is merely exemplary and other configurations of the first track 1406 and second track 1408 are envisioned.

FIG. 15 shows the transfer blocks 1404, the first track 1406, the second track 1408, and the coupler 1410 in greater detail. In the exemplary figure, the first track 1406 and the second track 1408 are positioned perpendicular to one another as to move a selected automated biologic processing unit 102 in both a first direction (e.g., horizontally) and a second direction (e.g., vertically). The first track 1406 is stationary relative to the housing 1402 of the automated selection and support structure 1400, and the second track 1408 is positioned at least partially and perpendicular at the first track 1406. The first track 1406 is able to move the second track 1408 along the length of the first track 1406, allowing for an operator to selectively control the position of the second track 1408 relative to the first track. Further, the coupler 1410 is positioned at the second track 1408, wherein, similarly to the relationship between the first track 1406 and the second track 1408, the second track 1408 is able to move the coupler 1410 along the length of the second track. In the exemplary embodiment shown in both FIG. 14 and FIG. 15, the first track 1406 is positioned perpendicular to the base 1403 of the housing 1402, and the second track 1408 is positioned at the first track 1406 and orientated parallel to the base. Therefore, as explained above, the second track 1408 is able to be moved vertically up and down the length of the first track 1406. Similarly, the coupler 1410 is positioned at the second track 1408 and is able to move horizontally along the length of the second track 1408. The speed at which the biologic processing unit 102 is moved along the first track 1406 and/or the second track 1408 may be controlled to ensure smooth motion and minimize disturbance to the activating, transducing, expanding, concentrating, and/or harvesting steps, of cell cultures therein.

In operation, the user may interact with an interface device 114 (e.g. computer, tablet, mobile device, etc.) positioned on the housing 1402 as to select one of the plurality of automated biologic processing units 102. Interface device 114 can be physically coupled to the system 1400 or remote from the system 1400 (i.e., handheld or otherwise movable) as described herein. The interface device 114 will navigate the coupler 1410 to the position of the selected automated biologic processing unit using the first track 1406 and the second track 1408. Once positioned, the coupler 1410 will mate with the transfer block 1404 associated with the selected automated processing unit 102. The second track 1408 will then navigate the coupler 1410, the transfer block 1404, and the automated biologic processing unit 102 horizontally until they are aligned with the first track 1406. The first track 1406 will then vertically translate the second track 1408 and, subsequently, the automated biologic processing unit 102 to the second position 120*b* to be presented to the user (see 1440 in FIG. 14). In order to return the automated processing unit 102 from the second position 120*b* back to the first position 120*a*, the process described may be reversed.

Figures 16, 17:
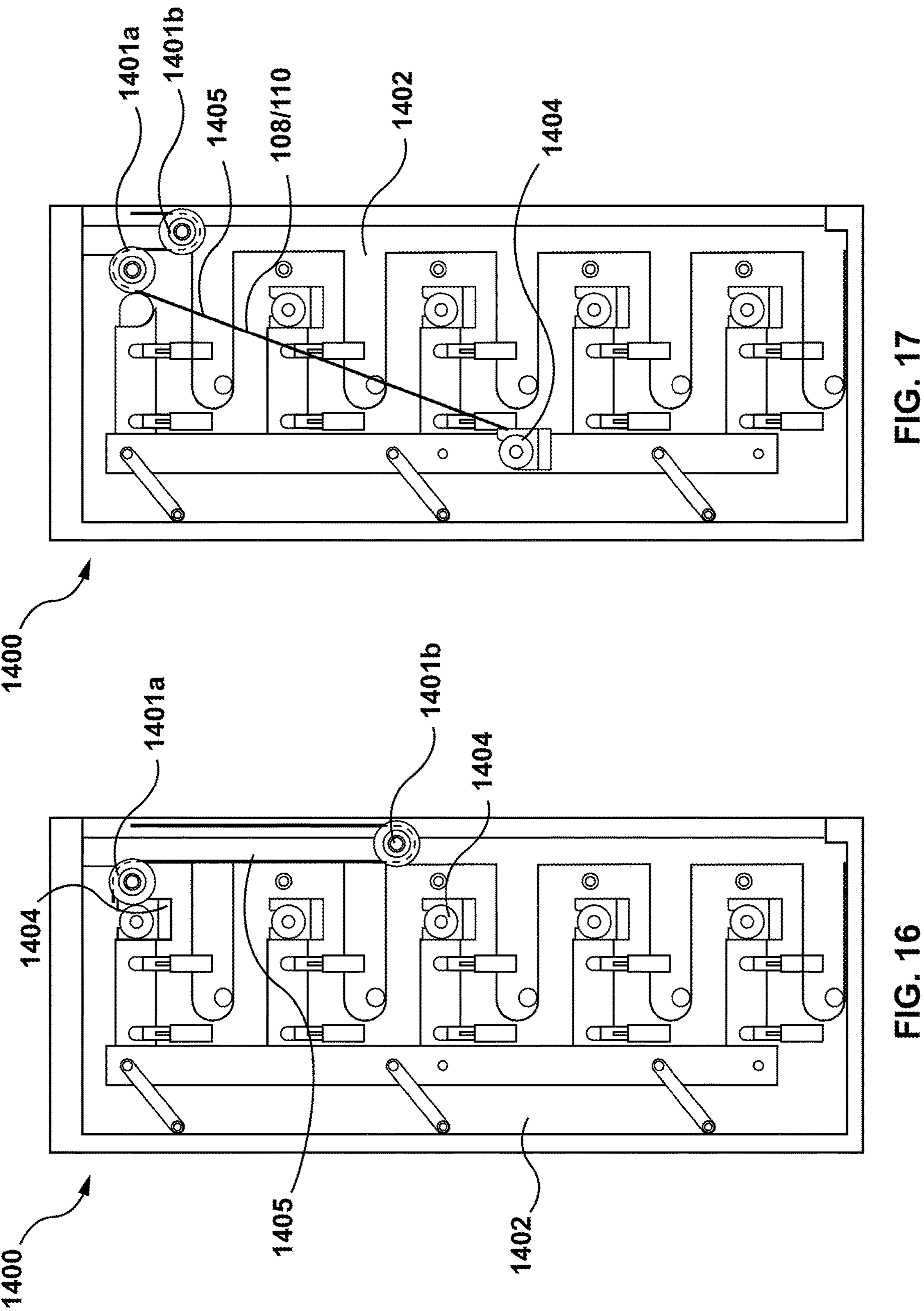
FIG. 16 depicts a side internal view of the fifth embodiment of an automated selection and support system of FIG. 14 while in a first position.
FIG. 17 depicts a side internal view of the fifth embodiment of an automated selection and support system of FIG. 14 while in a second position.

The housing 1402 encompasses the mechanics required to operate and move the first track 1406, the second track 1408, the coupler 1410, an electronic system as described in previous embodiments, a gas supply system as described in previous embodiments, and any ventilation or heat management components that may be necessary. The housing 1402 includes a base 1403 that is located at the bottom of the housing 1402. As shown in FIG. 16 and FIG. 17, the housing 1402 includes the electrical system 108 and the gas supply system 110 operably coupled (i.e. connected to allow for electric power, control, data transfer, and gas supply and return) to each of the plurality of biologic processing units 102 through a connection conduit 1405. The connection conduit 1405 moves and is configured to stay attached and follow each of the automated biologic processing units 102 as the automated biologic processing unit transitions from the first position 120*a* to the last position. FIGS. 16 and 17 show the configuration of the electrical system 108 and the gas supply system 110 for a singular biologic processing unit 102. Additional electrical supply systems and gas supply systems for the additional biologic processing units 102 can be arranged in a similar matter.

In embodiments, the electrical system 108 and/or gas system 110 may connect to each of the plurality of biologic processing units 102 via a single axis of connection. For example, FIG. 16 shows the connection conduit 1405, connecting the electrical system and gas supply system connected to the singular biologic processing unit 102 in the first position 120*a*, while FIG. 17 shows the connection conduit 1405 connecting the singular biologic processing unit 102 in the second position 120*b*. As shown, the connection conduit 1405 maintains the connection between the biologic processing unit 102 and the electrical system 108 and the gas supply system 110 while the automated biologic processing unit 102 transitions between the first position 120*a* and the last position. In embodiments, each biologic processing unit 102 is coupled by a connection conduit 1405 to the electrical system 108 and the gas supply system 110 in a similar manner as is shown in FIG. 16 and FIG. 17. As noted, each processing unit 102 may be fed by its own electrical system and gas supply system, so that appropriate changes can be made to the electricity and/or gas provided to individual processing units 102 as desired or required.

When a biologic processing unit 102 translates from the first position 120*a* to the second position 120*b*, as shown across FIGS. 16-17, the connection conduit 1405 connected to said biologic processing unit 102 will travel with it. For example, moving the biologic processing unit 102 via the first track 1406 and second track 1408 may cause the connection conduit 1405 to be pulled with the biologic processing unit 102. As shown in FIG. 16, a first guide 1401*a* is disposed adjacent to the transfer block 1404 of the desired biologic processing unit 102 that will be translated from the first position 120*a* to the second position 120*b*. As the transfer block 1404 translates, it pulls the connection conduit 1405 with it, directed via the first guide 1401*a* and a second guide 1401*b* disposed within the housing 1402. As the transfer block 1404 continues to pull the connection conduit 1404, the second guide 1401*b* begins to translate in a direction towards the first guide 1401*a* so as to provide enough slack on the connection conduit 1405, allowing the biologic processing unit 102 to complete its movement towards the second position 120*b* without excessive tension building on the connection conduit 1405, as exemplified in FIG. 17. The first track 1406 and second track 1408 may therefore receive the connection conduit 1405 on, within, or around themselves in a manner that would prevent any interruption of the connections from electrical supply system 108 and gas supply system 110 to the biologic processing unit 102. For example, the connection conduit 1405 may be pulled through or over the first track 1406 and second track 1408 via the first guide 1401*a* and second guide 1401*b* so as to allow for easier translation of the connection conduit 1405 and prevent pinching, kinking, disconnection, or general damage of the connection conduit 1405.

Similar to the embodiments described above, a heat management system 112, as shown in FIGS. 14-17, may be included in the automated selection and support system 1400. The heat management system 112 may be positioned either internally or externally in relation to the automated selection and support structure 1400. The heat management system 112 is configured to keep each of the automated biologic processing units 102 at a relatively consistent temperature (e.g. ±5° C.). As stated previously, the automated biologic processing units 102 require a consistent temperature in order to operate properly. It is envisioned that each automated biologic processing unit 102 may produce heat, and in some embodiments, the heat management system 112 may be used to remove any heat from each of the automated biologic processing units 102. As stated above, the heat management system 112 may be placed externally relative to the automated support and selection structure 1400. For example, multiple automated selection and support systems 1400 may be positioned in a temperature-controlled room, wherein the heat management system 112 may configured to control the temperature of the room or provide live data regarding the temperature of the units 102 to an external ventilation system. When positioned internally, the ventilation systems 112 may us a plurality of fans to either push or pull ambient air across the surface of each of the automated biologic processing units 102, or a fluid-based heat management system having fluid pathways to each from each biologic processing unit 102 connecting via conduit 1405, as described herein.

Figure 18:
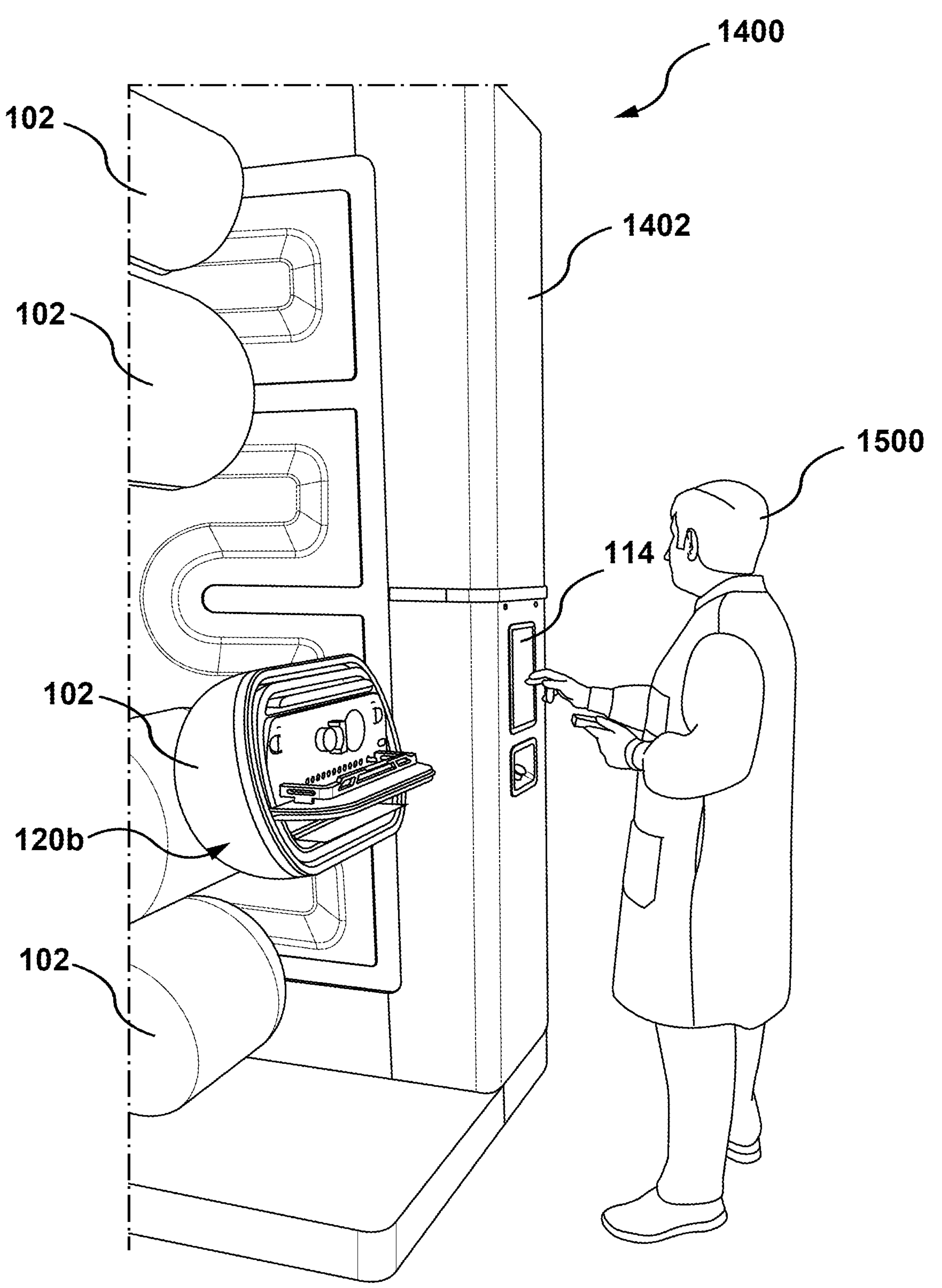
FIG. 18 depicts a perspective view of an end user interaction with the fifth embodiment of an automated selection and support system of FIG. 14, with an automated biologic processing unit in the second position.

FIG. 18 exemplifies an end user 1500 interaction with the fifth embodiment of the automated selection and support system 1400. The end user 1500 interacts with the interface device 114 disposed on the housing 1402 (or in embodiments, a remote/separate interface device 114 (not shown)) and inputs a command to translate the biologic processing unit 102 from the first position 120*a* to the second position 120*b*, consistent with embodiments described herein. In the second position 120*b*, the biologic processing unit 102 is positioned in a manner that allows for easy access by the end user 1500—i.e. in a position level at a point between the knees and the head of the end user 1500. The end user 1500 may then perform the tasks desired on the biologic processing unit 102 while in the second position 120*b*, and when complete, input a command via the interface device to return the biologic processing unit 102 back to the first position 120*a*, as exemplified in FIG. 19. Throughout this procedure of translating the biologic processing unit 102 from the first position 120*a* to the second position 120*b*, then back to the first position 120*a*, the biologic processing unit 102 can maintain its automated functions, dictated by the heat management system 112, the interface device 114, and/or a system architecture 800 as described in greater detail herein.

Figure 19:
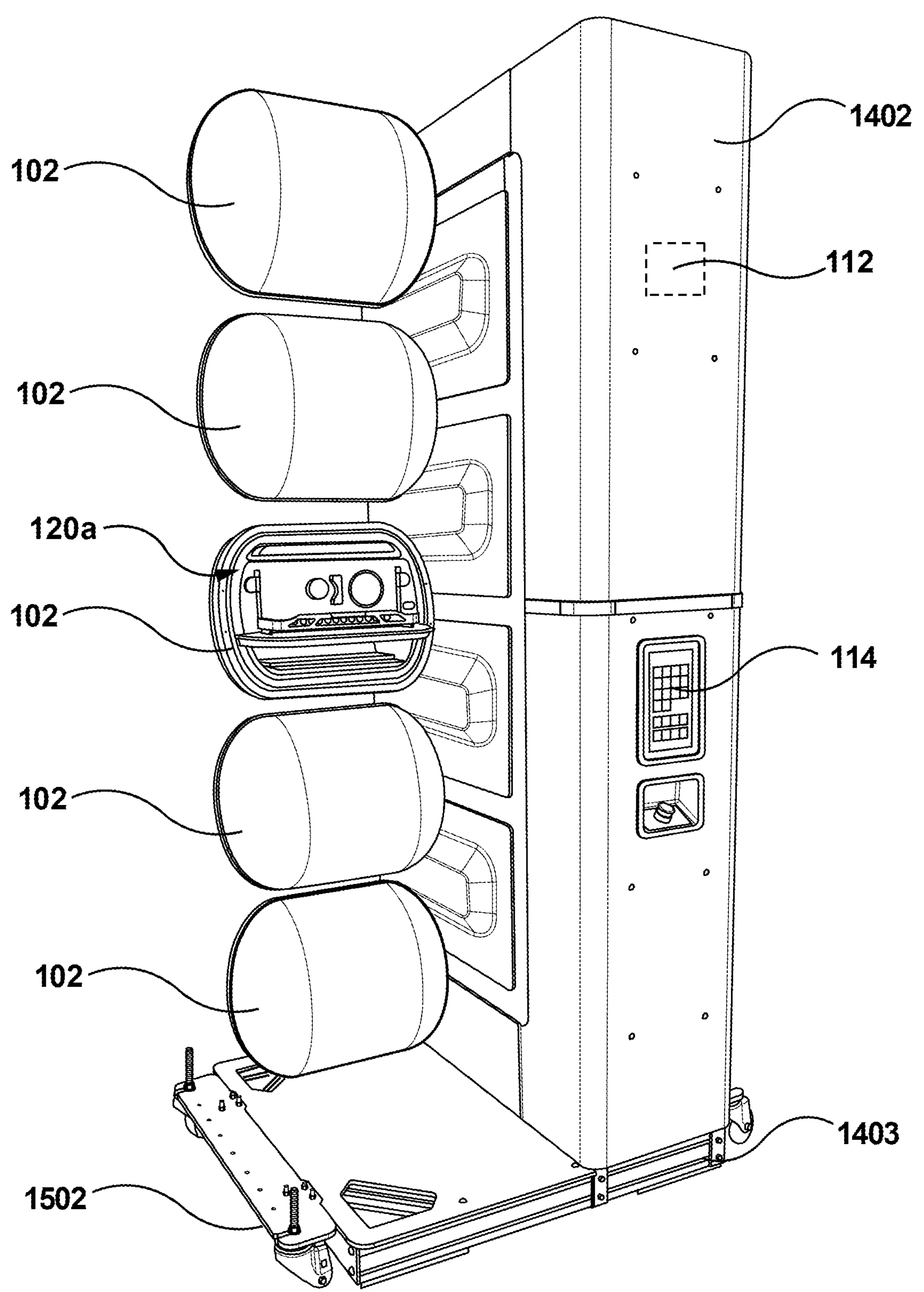
FIG. 19 depicts another perspective view of the fifth embodiment of an automated selection and support system of FIG. 14 with an open automated biologic processing unit.
Figure 20:
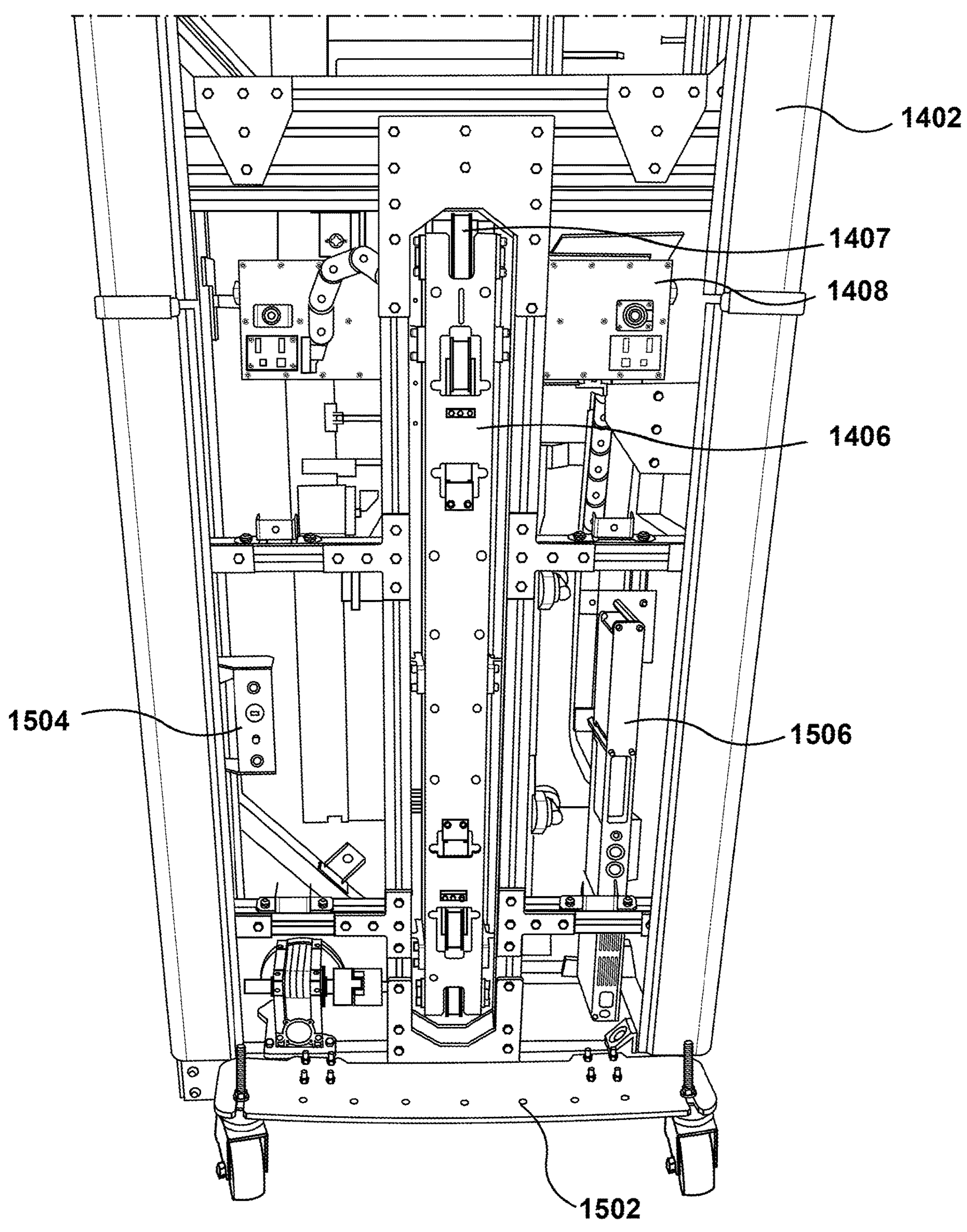
FIG. 20 depicts a side view of the fifth embodiment of an automated selection and support system of FIG. 14.

FIGS. 19 and 20 further depict a transport platform 1502 disposed on the base 1403 of the housing 1402. In embodiments, the transport platform 1502 may incorporate elements to move the entire housing 1402 of the automated selection and support system 1400, such as, but not limited to, wheels, tracks, ball bearings, and the like. The transport platform 1502 may be raised or lowered from a stationary position to a moving position, where the elements are out of contact with the ground/in contact with the ground, respectively. In the moving position, the transport platform 1502 allows for easy relocation of the housing 1402 within a clinical or hospital setting, or other cell therapy engineering manufacturing environment. Once in a desired location, the transport platform 1502 may be raised to the stationary position to secure the housing 1402 in place, and prevent any unwanted movement from the desired location. The transport platform 1502 may also include elements to lock or secure the housing to the floor, including various screws, pins, etc. In embodiments, the transport platform 1502 may be removable or disconnected entirely from the base 1403 of the housing 1402 once the housing 1402 is in the desired location. Once the transport platform 1502 is removed, the base 1403 may include elements to lock or secure the housing 1402 to the floor, including various screws, pins, etc.

FIG. 20 further exemplifies a side view of the automated selection and support system 1400, with the internal components partially exposed. The first track 1406 and the belt 1407 are shown in engagement with the second track 1408, all within the housing 1402. The second track 1408 is shown disposed near the top of the first track 1406, either to engage with the transfer block 1404 of the desired biologic processing unit 102 to be translated to the second position 120*b*, or to return the desired biologic processing unit 102 to the first position 120*a*. This position of the second track 1408 is consistent with the track positioning shown in FIG. 17 and further described in detail herein. A pushbutton enclosure 1504 may be disposed on the side of or within the housing 1402, and include several means of hardware interactivity, such as a main power switch, a seal release switch, a cassette release switch, a power outlet, a data outlet (such as a coax connection or ethernet connection), a USB port, a fiber optic port, a gas connection port, and the like. A chassis 1506 may further be provided on or within the housing 1402, and provide further ethernet, gas, or electrical connectivity capabilities. In embodiments, the chassis 1506 may house a breaker switch, motherboard, processing unit, router, modem, or means for data storage (e.g. HDD, SSD, etc.).

Figure 21:
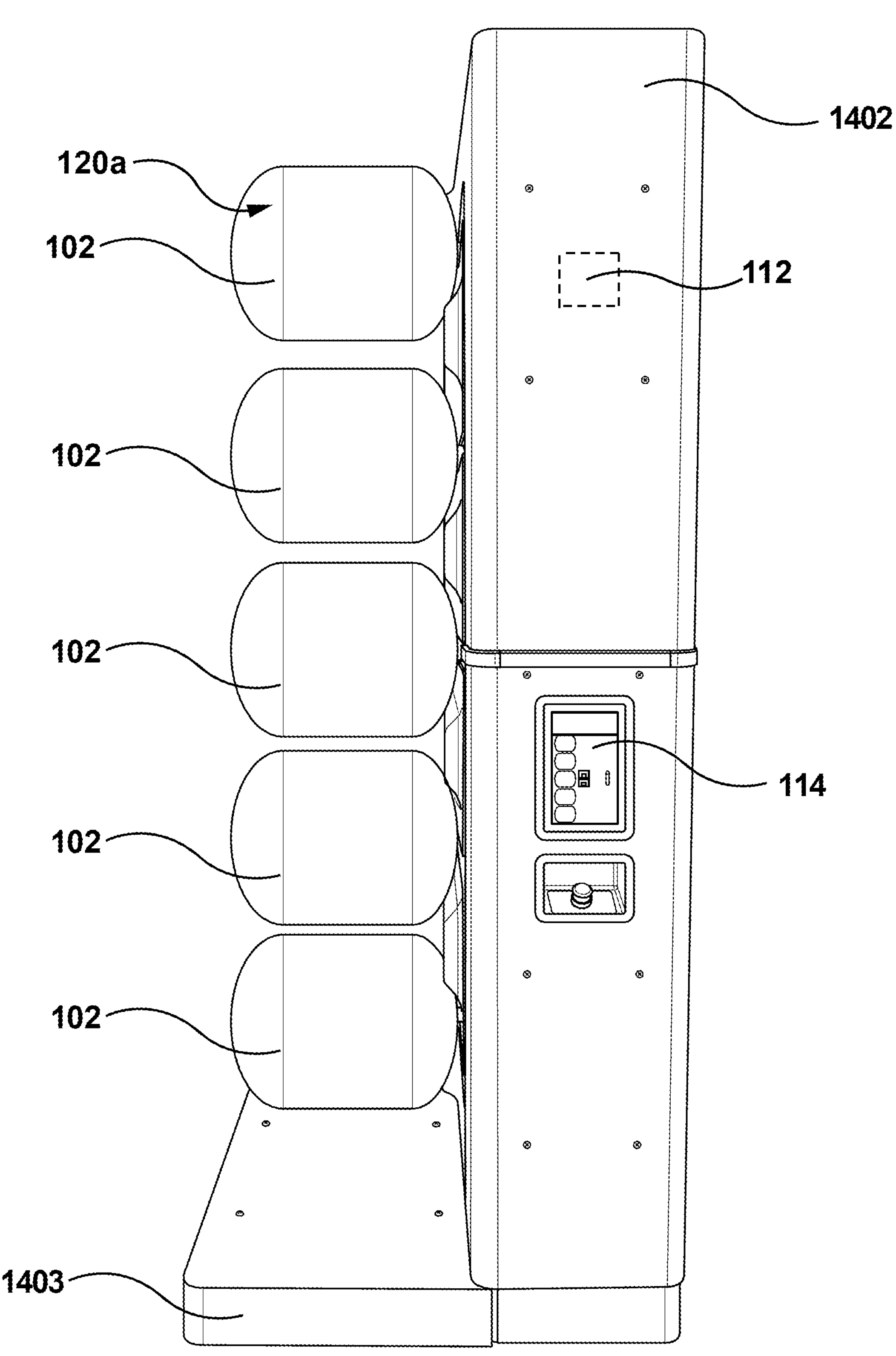
FIG. 21 depicts a front elevational view of the fifth embodiment of an automated selection and support system of FIG. 14.
Figure 22:
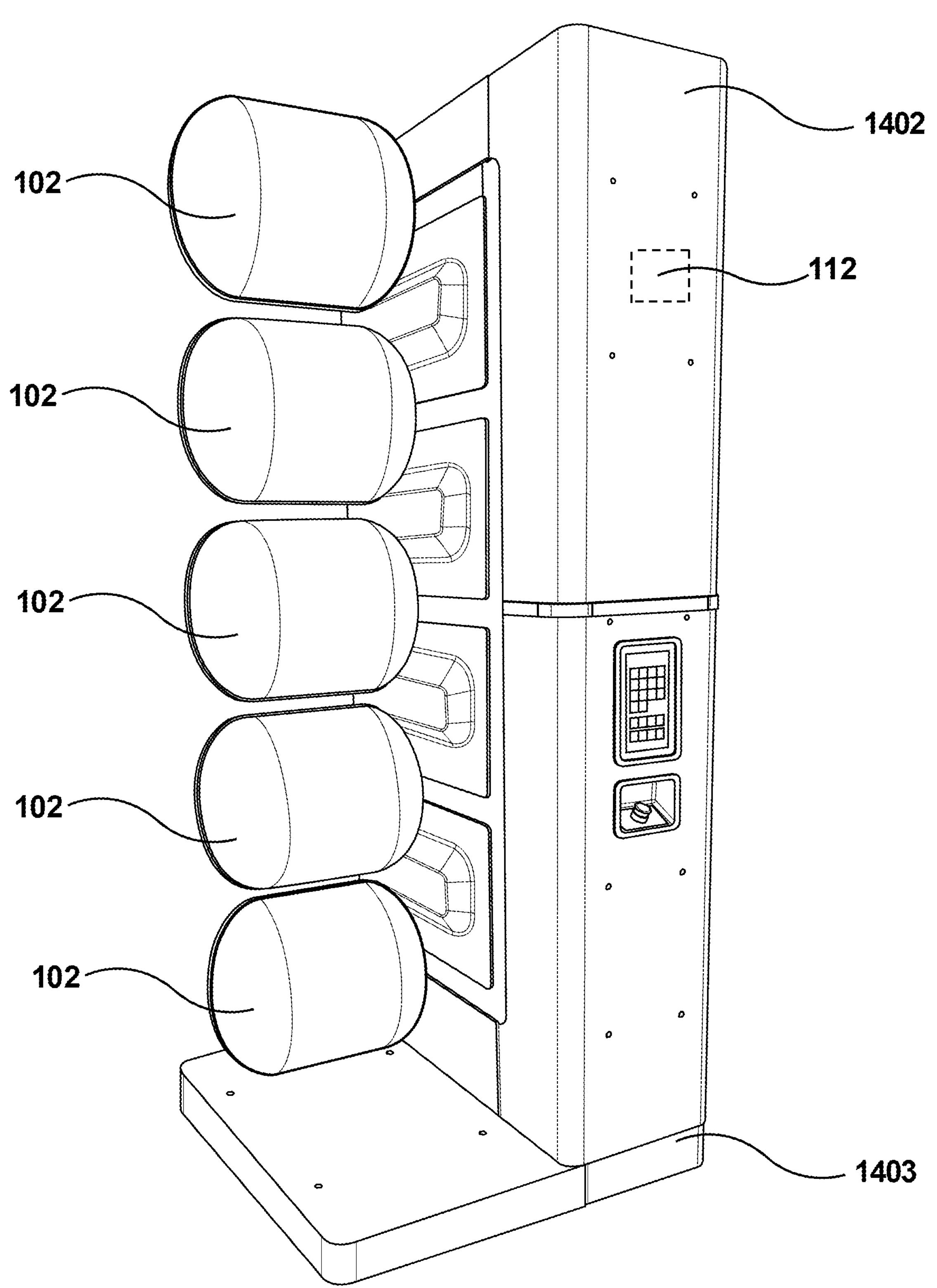
FIG. 22 depicts another perspective view of the fifth embodiment of an automated selection and support system of FIG. 14.

FIGS. 21 and 22 exemplify further elevational and perspective views, respectively, of the automated selection and support system 1400, with the plurality of biologic processing units 102 in the first position 120*a*. Each biologic processing unit 102 may operate and be translated between the first position 120*a* and the second position 120*b* independently (as previously shown in FIGS. 18 and 19), allowing for optimization of space utilization while simultaneously maintaining usability of the biologic processing units 102. The heat management system 112 may be disposed on or within the housing 1402, or as a separate component outside the housing 1402 (not shown). FIGS. 21 and 22 show an embodiment of the transport platform 1502 connected to the base 1402 in the stationary position, retracted within the base 1402 (and not visible in FIGS. 21 and 22).

Figure 23A:
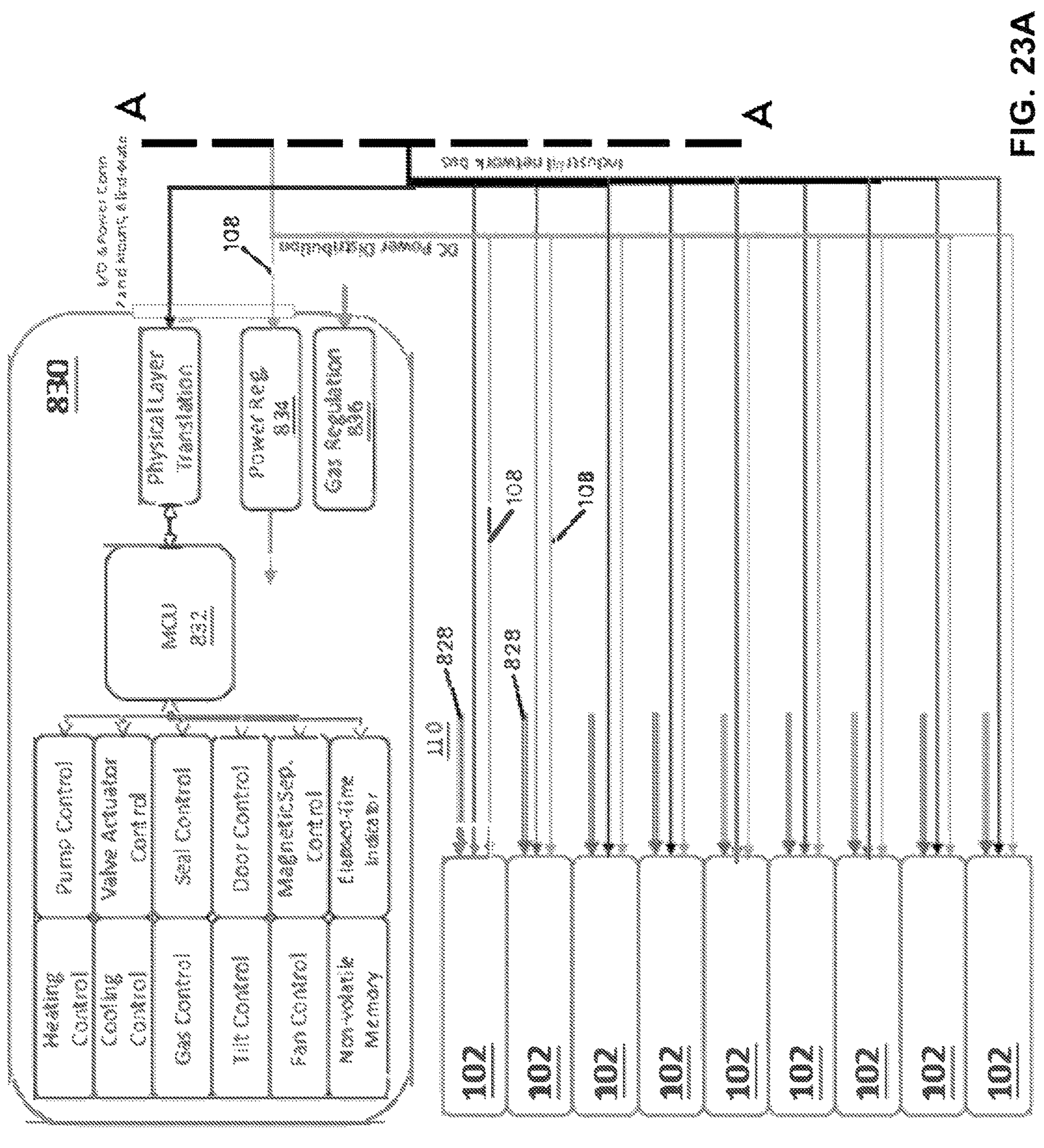
FIG. 23A depicts one half of an exemplary system and architecture for performing or facilitating the automated selection and support system according to embodiments hereof, divided by line A-A.
Figure 23B:
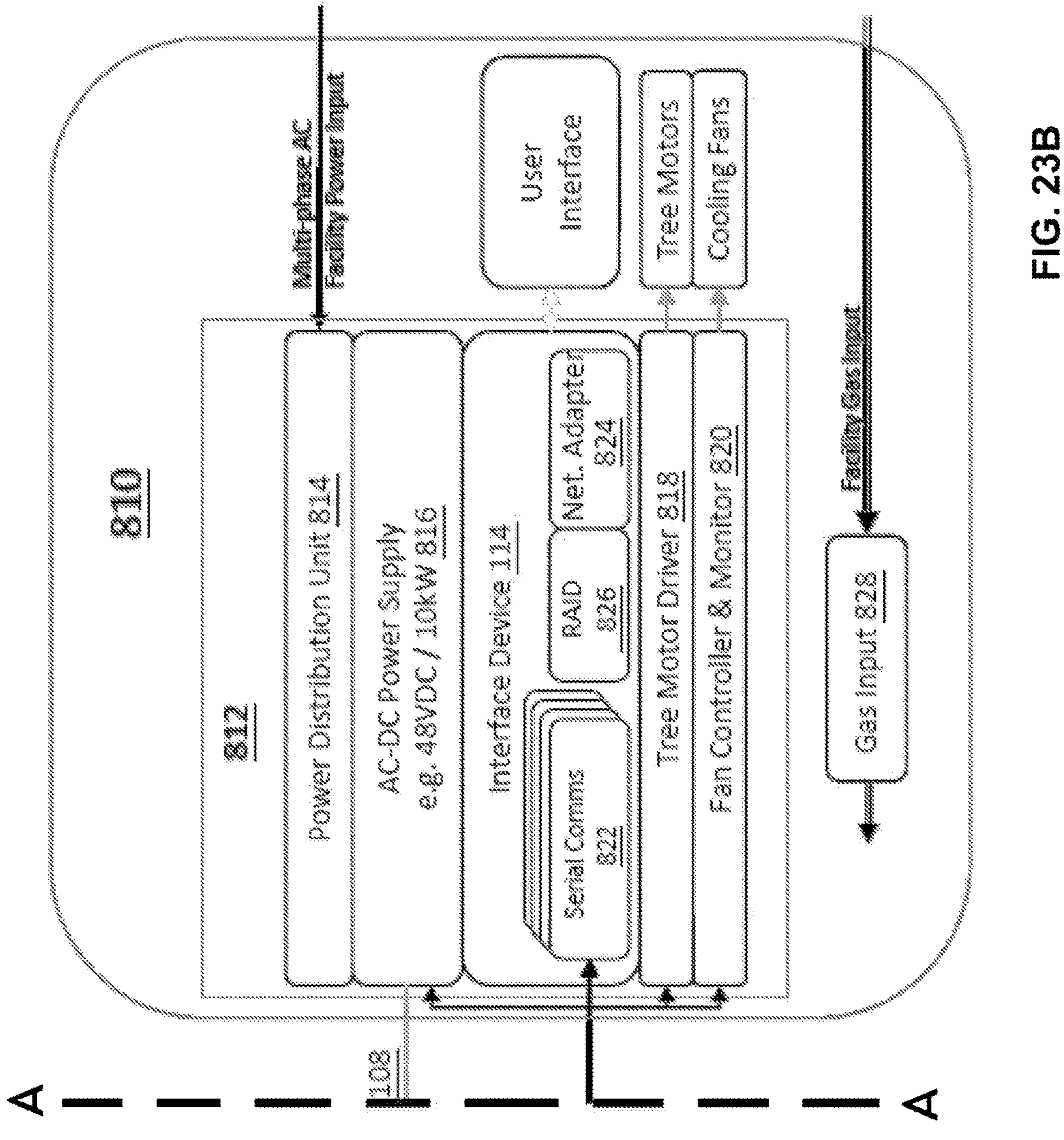
FIG. 23B depicts the second half of an exemplary system and architecture for performing or facilitating the automated selection and support system according to embodiments hereof, divided by line A-A.

FIGS. 23A and 23B illustrates an embodiment of the system architecture 800 for the automated selection and support systems 100/200/600/1000/1400 described herein, divided by line A-A. In embodiments, the system architecture 800 includes housing centralized functions 810 and biologic processing unit centralized functions 830. The housing centralized functions 810 may include a rack mounting 812 disposed on the housing 106/206/606/1006/1402 of the respective automated selection and support systems 100/200/600/1000/1400 described herein for receiving/holding various components and technologies, such as a power distribution unit 814, a power supply 816, a tree (system) motor driver 818, a fan controller/monitor 820, and/or the interface device 114, among other things. In embodiments, the electrical system 108 may include the power distribution unit 814, power supply 816 and/or the interface device 114, operatively connected and responsible for providing electrical energy to each of the plurality of biologic processing units 102, to the tree motor driver 818 and/or tree motors, to the fan controller/monitor 820 and/or cooling fans, to the interface device 114, and/or to any other electrical device disposed on, in, or near the housing 106/206/606/1006/1402 of the respective automated selection and support systems 100/200/600/1000/1400 described herein.

In embodiments, the gas supply system 110 may include a gas input 828 for providing gas to each of the plurality of biologic processing units 102 through the housing 106/206/606/1006/1402 of the respective automated selection and support systems 100/200/600/1000/1400 described herein. In embodiments, the interface device 114 may include a serial communicator 822, including but not limited to a CAN Bus or RS-485 Bus, a network adapter/connector 824 (such as a PCIe card), and/or a storage device 826, including, but not limited to, an electronic storage device, a magnetic storage device, an optical storage device, an electromagnetic storage device, a semiconductor storage device, or any suitable combination thereof. The storage device may form, e.g., a computer diskette, a hard disk drive (HDD), a solid-state drive (SDD), a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), and/or a memory stick. In embodiments, the storage device 826 may include data storage virtualization technologies, such as redundant array of independent disks (RAID).

In general, the housing centralized functions 810 may provide energy, communications, data, and/or any other necessary resources to the biologic processing unit centralized functions 830. In embodiments, the biologic processing unit centralized functions 830 may include a power regulator 834, a gas regulator 836, and/or a multipoint control unit (MPU) 832. For example, the MPU 832 of each individual biologic processing unit 102 may include or be capable of executing/controlling several functions on or within the respective biologic processing unit 102, including but not limited to: heating/cooling control, gas control, tilt control (with respect to the orientation of each of the plurality of biologic processing units 102), fan control, data memory (i.e. non-volatile), pump control, valve actuator control, seal control, door control, magnetic separation control, and/or elapsed time indication, among other functionalities. These functions/features of each biologic processing unit 102 may be autonomous, such that each biologic processing unit 102 may individually regulate and adjust these various features to maintain a desired environment within the biologic processing unit 102.

As the biologic processing units 102 automatically adjust over time, data is created and stored on the data memory. Data collected and stored by the memory of each of the plurality of biologic processing unit's 102 centralized functions 830 may be updated in real time and accessible via the interface device 114, or remotely via wired or wireless LAN connection, as further described herein. In embodiments, the data may include measured power supply (e.g. in watts), measured gas supply (e.g. in cubic feet or cubic meters), gas concentration, status of samples of cells, number of cells in sample, measured amount of sample (e.g. in liters), temperature within the biologic processing unit 102, automated temperature adjustments, automated power adjustments, automated gas supply adjustments, status of the pumps, valves, seals, door, fan(s), motors, motor drivers, gas regulators, electroporation activities, and/or magnetics (e.g. on or off; open or shut; active or inactive, etc.), logged end user inputs, angle of tilt of the biologic processing unit 102, elapsed time, and/or any other information pertaining to the biologic processing unit 102, the samples of cells, the housing 106/206/606/1006/1402 of the respective automated selection and support systems 100/200/600/1000/1400 and its various components as described herein.

In embodiments, the electrical system 108 and/or gas system 110 may connect to each of the plurality of biologic processing units 102 via a single axis of connection. For example, electricity and gas may be supplied from the housing centralized functions 810 to each of the plurality of biologic processing units 102 at or through a single point, such as the location of each biologic processing unit's 102 respective transfer block 1404 or coupler 1410. In embodiments, the single axis of connection may be established anywhere on or within the body of the biologic processing unit 102.

Figure 24:
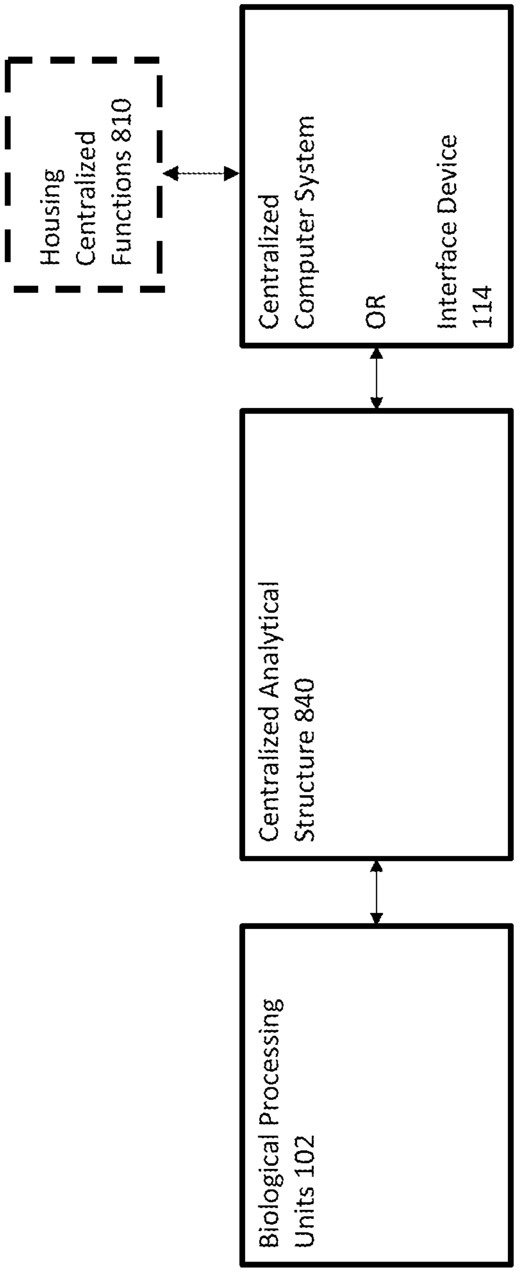
FIG. 24 depicts an exemplary system for an integrated and centralized analytical platform for use with the automated selection and support system embodiments described herein.

In an exemplary embodiment depicted in FIG. 24, the automated selection or support systems 100/200/600/1000/1400 may further include a centralized analytical structure 840 for the collection, analysis, and presentation of data from each individual biologic processing unit 102 in an automated fashion. Each biologic processing unit 102 may be connected to the centralized analytical structure 840 via a sterile, closed fluidic tubing that would transport samples of cells, cellular material, and/or culture medium to the centralized analytical structure 840 platform for processing and evaluation. In embodiments, centralized analytical structures 840 may be disposed within each of the biologic processing units 102. The transported samples may then be analyzed to to provide metrics on variables including, but not limited to, cell enumeration, cell viability, cell phenotype, dissolved gas concentrations, cell activation state, transduction efficiency, transfection efficiency, potency, cytokine secretion, metabolites, sterility, and/or endotoxin analysis. Exemplary analytical structures include various instruments such as spectrometers (UV/VIS, mass, etc.), particle size analyzers, fluorescence-based analysis (e.g., fluorometers, FACS, etc.), absorbance spectrometers, etc. These generated metrics may be automatically fed as data to a centralized computer system including or separate from the interface device 114 for display to an end user. As such, the interface device 114 may provide automatically updating data concerning the above determined metrics for each sample provided from each of the plurality of biologic processing units 102. In embodiments, the centralized computer system or interface device 114 may be integral with the centralized analytical structure 840 (not shown). The centralized computer system or interface device 114 may further include connectivity to the housing centralized functions 810.

Standard in-line analytical configurations may require a 1:1 ratio of manufacturing platform (e.g. biologic processing unit 102) to centralized analytical structure 840. For example, each biologic processing unit 102 may require their own separate analytical structure 840 for monitoring and providing the metrics/data previously described herein, or the analytical structure can be used for multiple biologic processing units. The present invention alternatively presents the centralized analytical structure 840 (or in embodiments, the housing centralized functions 810) configured to provide an X:1 ratio of biologic processing units 102 (represented as value X, wherein value X may be one, two, three, four, five, six, seven, eight, nine, or ten) to the centralized analytical structure 840 or housing centralized functions 810. The advantages of integrating the centralized analytical structure 840 may include reduced hardware and/or software costs, increased ease of hardware/software maintenance, increased batch consistency, reduced batch failure potential, and simplified release testing processes, among other benefits.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with.

Further embodiments include:

Embodiment 1 is an automated selection and support system comprising: a plurality of automated biologic processing units, each of the plurality of automated biologic processing units being translatable between at least a first position for storage and maintaining the plurality of automated biologic processing units, and a second position for presenting at least one or more of the plurality of automated biologic processing units; a movable support structure for transitioning each of the plurality of automated biologic processing units between the first position and the second position; an electrical system including a power supply and an interface device, both the power supply and the interface device being operatively connected to each of the plurality of automated biologic processing units and the movable support structure; and a gas supply system including a gas line fluidly coupled to each of the plurality of automated biologic processing units.

Embodiment 2 is the system of embodiment 1, wherein the electrical system and gas supply system are both operatively connected to each of the automated biologic processing units via a single axis of connection.

Embodiment 3 is the system of embodiment 1 or embodiment 2, wherein the plurality of biologic processing units are translatable to a plurality of positions between the first position for storage and maintaining, and the second position for presenting the at least one or more of the plurality of automated biologic processing units.

Embodiment 4 is the system of any one of embodiments 1 to 3, wherein the plurality of biologic processing units are autonomous such that each of the plurality of biologic processing units individually regulate and adjust various functions and controls to maintain a desired environment within each of the plurality of automated biologic processing units in real time.

Embodiment 5 is the system of embodiment 4, wherein the various functions and controls include heating control, cooling control, gas control, tilt control, fan control, data memory, pump control, valve actuator control, seal control, door control, magnetic separation control, and/or elapsed time indication.

Embodiment 6 is the system of any one of embodiments 1 to 5, wherein translating at least one of the plurality of automated biologic processing units does not impact an activating, transducing, expanding, concentrating, and/or harvesting steps of cell cultures within the remaining plurality of automated biologic processing units.

Embodiment 7 is the system of embodiment 1, further comprising a heat management system configured to circulate a fluid to heat or cool each of the plurality of automated biologic processing units.

Embodiment 8 is the system of embodiment 7, wherein the heat management system circulates the fluid within the interior of each of the plurality of automated biologic processing units.

Embodiment 9 is the system of any one of embodiments 1 to 8 wherein the interface device is a separate unit allowing for remote access/connection.

Embodiment 10 is the system of any one of embodiments 1 to 8, wherein the interface device is physically coupled to the system.

Embodiment 11 is the system of any one of embodiments 1 to 10, wherein the electrical system operably controls the movable support structure such that the automated biologic processing unit is maintained in a level position while transitioning between the first position and second position.

Embodiment 12 is the system of embodiment 11, wherein the electrical system operably controls the movable support structure such that any fluids in a biologic process chamber in an interior of the automated biologic processing unit are maintained in a static or laminar state during the transition from the first position to the second position.

Embodiment 13 is an automated selection and support system comprising: a plurality of automated biologic processing units, each of the plurality of automated biologic processing units having a first position for storage and maintaining the plurality of automated biologic processing units, and a second position for presenting the automated biologic processing unit to a user; a plurality of swing arms, each swing arm including: a first end operatively coupled to one automated biologic processing unit from the plurality of automated biologic processing units; and a second end operatively coupled to a drive motor, the drive motor configured to rotate the swing arm to transition the automated biologic processing unit between the first position and the second position, wherein the swing arm maintains the automated biologic process unit rotationally level; an electrical system including a power supply and an interface device, both operatively coupled to each of the automated biologic processing units and the drive motor; and a gas supply system including a gas line fluidly coupled to each of the plurality of automated biologic processing units.

Embodiment 14 is the system of embodiment 13, wherein the drive motor is operatively coupled to the second end of the swing arm via an active control device, the second end further including a gear.

Embodiment 15 is the system of embodiment 13 or embodiment 14, wherein the first end of the swing arm includes a pivot point to maintain the automated biologic processing unit rotationally level.

Embodiment 16 is the system of any of embodiments 13 to 15, further including a heat management system configured to circulate a fluid to heat or cool each of the plurality of automated biologic processing units.

Embodiment 17 is the system of any one of embodiments 13 to 16, wherein the electrical system, the gas supply system, and/or the heat management system are positioned within a housing supporting the plurality of swing arms.

Embodiment 18 is the system of embodiment 16, wherein the heat management system circulates the fluid within the interior of each of the plurality of automated biologic processing units.

Embodiment 19 is the system of any one of embodiments 13 to 16, wherein the electrical system and gas supply system are both operatively connected to each of the automated biological processing units via a single axis of connection.

Embodiment 20 is an automated selection and support system comprising: a plurality of automated biologic processing units, each of the plurality of automated biologic processing units having a first position for storage and maintaining the plurality of automated biologic processing units, and a second position for presenting the automated biologic processing unit to a user; a plurality of vertical rails; a gantry configured to move on the vertical rails and select one of the automated biologic processing units and transition the automated biologic processing unit between the first position and the second position; an electrical system including a power supply and an interface device both operatively coupled to each of the automated biologic processing units; and a gas supply system including a gas line fluidly coupled to each of the plurality of automated biologic processing units, wherein the vertical rails, the electrical system, the gas supply system, and/or a heat management system are enclosed within a housing.

Embodiment 21 is the system of embodiment 20, wherein the gantry comprises at least two horizontal sliders.

Embodiment 22 is the system of embodiment 20 or embodiment 21, comprising four vertical rails.

Embodiment 23 is the system of any one of embodiments 20 to 22, further comprising a plurality of holding shelves configured to hold each of the automated biologic processing units, wherein the gantry is further configured to selectively couple to a single holding shelf of the plurality of holding shelves.

Embodiment 24 is the system of embodiment 23, wherein the gantry is further configured to independently move the single holding cell both horizontally and vertically.

Embodiment 25 is an automated selection and support system comprising: a plurality of automated biologic processing units, each of the plurality of automated biologic processing units having a first position for storage and maintaining the plurality of automated biologic processing units, and a second position for presenting the automated biologic processing unit to a user; a plurality of modular holding cells configured to each hold one of the automated biologic processing units; a shuttle configured to travel between each of the modular holding cells to select one of the automated biologic processing units and transition the automated biologic processing unit between the first position and the second position; an electrical system including a power supply and an interface device, both operatively coupled to each of the automated biologic processing units; and a gas supply system including a gas line fluidly coupled to each of the plurality of automated biologic processing units, wherein the electrical system, the gas supply system, and/or a heat management system are enclosed within a housing.

Embodiment 26 is the system of embodiment 25, further including a plurality of chassis, each chassis positioned within a single holding cell and configured to support one of the automated biologic processing units and transition the automated biologic processing unit between the first position and the second position.

Embodiment 27 is the system of embodiment 26, wherein the shuttle is configured to selectively couple to each of the chassis.

Embodiment 28 is the system of embodiment 27, wherein the shuttle is configured to independently move the chassis both horizontally and vertically relative to the modular holding cells.

Embodiment 29 is the system of any one of embodiments 25 to 28, wherein the interface device of the electrical system is positioned in the shuttle.

Embodiment 30 is an automated selection and support system comprising: a plurality of automated biologic processing units, each of the plurality of automated biologic processing units having a first position for storage and maintaining the plurality of automated biologic processing units, and a second position for presenting the automated biologic processing unit to a user; a plurality of transfer blocks, each transfer block being configured to couple to an automated biologic processing unit of the plurality of automated biologic processing units; a coupler configured to mate with one of the blocks of the plurality of blocks; a first track configured to move the coupler in a first direction; a second track configured to move the first track in a second direction, wherein the second track is substantially perpendicular to the first track; an electrical system including a power supply and an interface device, both operatively connected to each of the plurality of automated biologic processing units and the transfer blocks; a gas supply system including a gas line fluidly coupled to each of the plurality of automated biologic processing units; and wherein the first track and second track are configured to move one of the plurality of automated biologic processing units from the first position to the second position.

Embodiment 31 is the system of embodiment 30, further including a housing having a first guide and a second guide disposed therein for guiding at least one of the power supply and/or the gas line connected to each of the plurality of automated biologic processing units through the housing.

Embodiment 32 is the system of embodiment 30 or embodiment 31, wherein the power supply line and gas line are connected to each of the plurality of automated biologic processing units via a single axis of connection.

Embodiment 33 is the system of any one of embodiments 30 to 32, wherein moving one of the plurality of automated biologic processing units from the first position to the second position does not impact an activating, transducing, expanding, concentrating, and/or harvesting steps of cell cultures within the remaining plurality of automated biologic processing units.

Embodiment 34 is the system of any one of embodiments 30 to 33, further comprising a heat management system configured to circulate a fluid to each of the plurality of automated biologic processing units.

Embodiment 35 is the system of embodiment 34, wherein the heat management system circulates the fluid within the interior of each of the plurality of automated biologic processing units.

Embodiment 36 is the system of any one of embodiments 30 to 35, wherein the interface device is a separate unit allowing for remote access/connection.

Embodiment 37 is the system of any one of embodiments 30 to 35, wherein the interface device is physically associated with the system.

Embodiment 38 is the system of any one of embodiments 30 to 37, wherein the plurality of biologic processing units are translatable to a plurality of positions, or nth positions between the first position for storage and maintaining, and the last position for presenting the at least one or more of the plurality of automated biologic processing units.

Embodiment 39 is the system of any one of embodiments 30 to 38, wherein the plurality of biologic processing units are autonomous such that each of the plurality of biologic processing units individually regulate and adjust various functions and controls to maintain a desired environment within each of the plurality of automated biologic processing units in real time.

Embodiment 40 is the system of any of the preceding embodiments, wherein each of the plurality of biologic processing units connect to a centralized analytical structure for collection, analysis, and presentation of metrics concerning samples transported from each of the plurality of biologic processing units to the centralized analytical structure.

Embodiment 41 is a method for presenting an automated biologic processing unit to a user, comprising: selecting an automated biologic processing unit from an automated selection and storage system, the automated selection and storage system including: a plurality of automated biologic processing units, each of the plurality of automated biologic processing units having a first position for storage and maintaining the automated biologic processing units, and a second position for presenting the automated biologic processing unit to a user; a movable support structure for transitioning each of the plurality of automated biologic processing units between the first position and the second position; an electrical system including a power supply and an interface device, both operatively connected to each of the plurality of automated biologic processing units and the movable support structure; and a gas supply system including a gas line fluidly coupled to each of the plurality of automated biologic processing units; transitioning the selected automated biologic processing unit from the first position to the second position using the movable support structure; and returning the selected automated biologic processing unit from the second position to the first position.

What is claimed is:

1. An automated selection and support system comprising:

a plurality of automated biologic processing units, each of the plurality of automated biologic processing units being translatable between at least a first position for storage and maintaining the plurality of automated biologic processing units, and a second position for presenting at least one or more of the plurality of automated biologic processing units;

a movable support structure for transitioning each of the plurality of automated biologic processing units between the first position and the second position;

an electrical system including a power supply and an interface device, both the power supply and the interface device being operatively connected to each of the plurality of automated biologic processing units and the movable support structure; and a gas supply system including a gas line fluidly coupled to each of the plurality of automated biologic processing units;

wherein the electrical system and the gas supply system are both operatively connected to each of the automated biologic processing units via a single axis of connection comprising a connection conduit, and the connection conduit is configured to travel with each automated biologic processing unit between the first position and the second position.

2. The system of claim 1, wherein the plurality of automated biologic processing units are translatable to a plurality of positions between the first position for storage and maintaining, and the second position for presenting the at least one or more of the plurality of automated biologic processing units.

3. The system of claim 1, wherein the plurality of automated biologic processing units are autonomous such that each of the plurality of automated biologic processing units individually regulate and adjust various functions and controls to maintain a desired environment within each of the plurality of automated biologic processing units in real time.

4. The system of claim 3, wherein the various functions and controls include heating control, cooling control, gas control, tilt control, fan control, data memory, pump control, valve actuator control, seal control, door control, magnetic separation control, and/or elapsed time indication.

5. The system of claim 1, wherein translating at least one of the plurality of automated biologic processing units does not impact an activating, transducing, expanding, concentrating, and/or harvesting steps of cell cultures within the remaining plurality of automated biologic processing units.

6. The system of claim 1, further comprising a heat management system configured to circulate a fluid to heat or cool each of the plurality of automated biologic processing units.

7. The system of claim 1 wherein the interface device is a separate unit allowing for remote access/connection.

8. The system of claim 1, wherein the interface device is physically coupled to the system.

9. The system of claim 1, wherein the electrical system operably controls the movable support structure such that each of the plurality of automated biologic processing units are maintained in a level position while transitioning between the first position and the second position.

* * * * *